US008728773B2

(12) United States Patent
Boy et al.

(10) Patent No.: US 8,728,773 B2
(45) Date of Patent: May 20, 2014

(54) FERMENTATIVE PRODUCTION OF ORGANIC COMPOUNDS USING SUBSTANCES CONTAINING DEXTRIN

(76) Inventors: Matthias Boy, Langen (DE); Stephan Freyer, Neustadt (DE)

( * ) Notice: Subject to any disclaimer, the term of this patent is extended or adjusted under 35 U.S.C. 154(b) by 993 days.

(21) Appl. No.: 12/094,646

(22) PCT Filed: Nov. 27, 2006

(86) PCT No.: PCT/EP2006/068927
§ 371 (c)(1),
(2), (4) Date: May 22, 2008

(87) PCT Pub. No.: WO2007/060234
PCT Pub. Date: May 31, 2007

(65) Prior Publication Data
US 2008/0318287 A1  Dec. 25, 2008

(30) Foreign Application Priority Data

Nov. 28, 2005  (DE) .......................... 10 2005 056 669

(51) Int. Cl.
*C12P 13/08* (2006.01)
*C12P 13/04* (2006.01)
*C12P 7/26* (2006.01)

(52) U.S. Cl.
USPC .......................................... 435/115; 435/148

(58) Field of Classification Search
USPC .......................................... 435/115, 106, 148
See application file for complete search history.

(56) References Cited

U.S. PATENT DOCUMENTS

| | | | | |
|---|---|---|---|---|
| 4,963,486 A | * | 10/1990 | Hang | 435/139 |
| 5,104,799 A | * | 4/1992 | Mothes et al. | 435/144 |
| 5,151,354 A | | 9/1992 | Strasser et al. | |
| 5,183,753 A | | 2/1993 | Wizani et al. | |
| 6,180,390 B1 | * | 1/2001 | Chu et al. | 435/252.1 |
| 6,451,567 B1 | | 9/2002 | Barclay | |
| 6,538,164 B1 | * | 3/2003 | Gallagher et al. | 568/871 |
| 6,569,646 B2 | | 5/2003 | Sengupta et al. | |
| 7,820,419 B2 | * | 10/2010 | Smith et al. | 435/161 |
| 2002/0079268 A1 | | 6/2002 | Caboche et al. | |
| 2006/0211101 A1 | | 9/2006 | Chotani et al. | |
| 2008/0032374 A1 | * | 2/2008 | Zelder et al. | 435/170 |
| 2008/0318287 A1 | | 12/2008 | Boy et al. | |
| 2009/0081749 A1 | * | 3/2009 | Verser et al. | 435/165 |

FOREIGN PATENT DOCUMENTS

| | | |
|---|---|---|
| CN | 1173541 | 2/1998 |
| CN | 1218111 | 6/1999 |
| CN | 1266102 | 9/2000 |
| CN | 1321772 A | 11/2001 |
| CN | 1415755 A | 5/2003 |
| EP | 0 171 218 | 2/1986 |
| EP | 0456033 A2 | 11/1991 |
| EP | 1205557 | 5/2002 |
| EP | 1957658 | 8/2008 |
| JP | 56-169594 | 12/1981 |
| JP | 57-159500 | 10/1982 |
| JP | 2001-072701 | 3/2001 |
| JP | 2001/275693 | 10/2001 |
| JP | 2001/309751 | 11/2001 |
| JP | 2003-164265 A | 6/2003 |
| JP | 2003-259892 A | 9/2003 |
| NL | 8302229 | 1/1985 |
| WO | WO-9206992 A2 | 4/1992 |
| WO | WO-02/077252 A1 | 10/2002 |
| WO | WO-2004/113551 A1 | 12/2004 |
| WO | WO-2005/089514 A2 | 9/2005 |
| WO | WO-2005/116228 | 12/2005 |
| WO | WO-2005118827 A2 | 12/2005 |
| WO | WO-2007/028804 | 3/2007 |

OTHER PUBLICATIONS

Modak et al. (General Characteristics of Optimal Feed Rate Profiles for Various Fed-batch Fermentation Processes. Biotechnology and Bioengineering, (1986) vol. XXVIII 1396-1407).*
Pfefferle, et al., "Biotechnological Manufacture of Lysine," *Advances in Biochemical Engineering*, vol. 79, pp. 59-112.
Beukema, et al. "Production of Fermentation Syrups by Enzymatic Hydrolysis of Potatoes," *Biotechnological Research in the Netherlands*, 6, 1983.
Mersmann, et al. "Selection and Design of Aerobic Bioreactors," Ehem. Eng. Technol., 13, 1990, pp. 357-370.
International Search Report for PCT/EP2006/068927, mailed Feb. 6, 2007.
International Preliminary Report on Patentability for International Application PCT/EP2006/068927, dated Jul. 8, 2008.

(Continued)

*Primary Examiner* — Karen Cochrane Carlson
*Assistant Examiner* — Natalie Moss
(74) *Attorney, Agent, or Firm* — Novak Druce Connolly Bove + Quigg LLP

(57) ABSTRACT

Process for the production of at least one organic compound having at least 3 C atoms or having at least 2 C atoms and at least 1 N atom by fermentation. In particular, the process comprises milling a starch feedstock, thus obtaining a millbase which comprises at least part of the nonstarchy solid constituents of the starch feedstock; suspending the millbase in an aqueous liquid and liquefying the millbase present in the aqueous liquid in the presence of at least one starch-liquefying enzyme, obtaining an aqueous dextrin-containing medium (1) which comprises at least a part of the nonstarchy solid constituents of the starch feedstock; and using the aqueous dextrin-containing medium (1) in a fermentation for culturing a microorganism which is capable of overproducing the organic compound; wherein enzymes which hydrolyze the dextrins to monosaccharides are being added in an amount of less than 0.001% by weight based on the total weight of the starch feedstock employed, or not at all.

20 Claims, No Drawings

(56) References Cited

OTHER PUBLICATIONS

Bailey, et al., "Production of *Pleospora papaveracea* biomass in liquid culture and its infectivity on opium poppy (*Papaver somniferum*)", Weed Science, vol. 52, (2004), pp. 91-97.

Benslimane, et al., "Influence of dextrins on the assimilation of yeast extract amino acids in culture of *Streptomyces ambofaciens* producer of spiramycin", Laboratory of Industrial and Nutritional Microbiology, (1995), pp. 1-11.

Erratt, et al., "Allelism within the DEX and STA gene families in *Saccharmoyces diastaticus*", Mol Gen Genet, vol. 202, No. 25002, (1986) pp. 255-256.

Kim, et al., "High-Efficieny, One-Step Starch Utlization by Transformed *Saccharomyces* Cells Which Secrete Both Yeast Gluoamylase and Mouse α-Amylase", Applied and Environmental Microbiology vol. 54, No. 4, (1988), pp. 966-971.

Miura, et al., "Production of L-Lactic Acid from Corncob", vol. 97, No. 3, (2004), pp. 153-157.

Nguyen, et al., "Optimisation of Composition of Media for the Production of Amyloytic Enzymes by *Thermomyces lanuginosus* ATCC 34626", Food technol. biotechnol., vol. 38, No. 3, (2000), pp. 229-234.

Taniguchi, et al., "Prodcution of L-Lactic Acid by Simultaneous Saccharification and Fermentation Using Unsterilized Defatted Ric Bran as a Carbon Source and Nutrient Components", Food Science Technol. Res., vol. 11, No. 4, (2005) pp. 400-406.

Waksman, et al., "Lactic Acid Production by Species of *Rhizopus*", New Jersey Agricultural Experiment Station, Vo. 59, (1937), pp. 545-547.

Wilke, D., "Raw materials for fermentation", Dr. Wilke & Partner Biotech Consulting, No. 6, pp. 115-128.

Skory, C.D., "Lactic Acid Production by *Rhizopus oryzae* Transformants with Modified Lactate Dehydrogenase Activity", Appl. Microbiol. Biotechnol., vol. 64, (2004), pp. 237-242.

Soccol, C.R., et al., "Production of L-Lactic Acid by *Rhizopus* Species", World Journal of Microbiology & Biotechnology, vol. 10, (1994), pp. 433-435.

Errat, J.A., et al., "Fermentation Studies Using *Saccharomyces diastaticus* Yeast Strains", Dev. Ind., Microbiol., vol. 22, (1981), pp. 557-589.

Heiss, R., Lebensmittel-technologie, Springer Verlag, (2004), pp. 360-381.

* cited by examiner

FERMENTATIVE PRODUCTION OF ORGANIC COMPOUNDS USING SUBSTANCES CONTAINING DEXTRIN

CROSS-REFERENCE TO RELATED APPLICATIONS

This application is a national stage application of PCT/EP2006/068927, filed Nov. 27, 2006, which claims priority of German Patent Application No. 102005056669.3, filed Nov. 28, 2005; the entire contents of all are hereby incorporated by reference.

The present invention relates to the fermentative production of organic compounds having at least 3 C atoms or having at least 2 C atoms and at least 1 N atom using, for culturing the microorganisms, a dextrin-containing medium which comprises at least part of the nonstarchy solid constituents of the starch feedstock.

Sugar-containing liquid media are a basic nutrient source for a multiplicity of fermentative processes; the sugar components which are present in the media are metabolized by the microorganisms employed, giving rise to organic products of value. The range of microbial metabolites thus prepared, i.e. organic compounds, comprises for example low-molecular-weight volatile compounds such as ethanol, nonvolatile metabolites such as amino acids, vitamins and carotenoids, and a multiplicity of further substances.

Depending on the various process conditions, different carbon feedstocks are exploited for such generally known microbial fermentative processes. They extend from pure sucrose via beet, and sugarcane molasses to what are known as high-test molasses (inverted sugarcane molasses) to glucose from starch hydrolyzates. Moreover, acetic acid and ethanol are mentioned as cosubstrates which can be employed on an industrial scale for the biotechnological production of L-lysine (Pfefferle et al., Biotechnological Manufacture of Lysine, Advances in Biochemical Engineering/Biotechnology, Vol. 79 (2003), 59-112).

Based on the abovementioned carbon feedstocks, various methods and procedures for the sugar-based, fermentative production of microbial metabolites are established. Taking L-lysine as an example, these are described for example by Pfefferle et al. (loc. cit.) with regard to strain development, process development and industrial production.

An important carbon feedstock for the microorganism-mediated fermentative production of microbial metabolites is starch. The latter must first be liquefied and saccharified in preceding reaction steps before it can be exploited as carbon feedstock in a fermentation. To this end, the starch is usually obtained in pre-purified form from a natural starch feedstock such as potatoes, cassava, cereals, for example wheat, corn, barley, rye, triticale or rice, and subsequently enzymatically liquefied and saccharified, whereafter it is employed in the actual fermentation for producing the desired metabolites.

In addition to the use of such pre-purified starch feedstocks, the use of non-pretreated starch feedstocks for the preparation of carbon feedstocks for the fermentative production of microbial metabolites has also been described. Typically, the starch feedstocks are initially comminuted by grinding. The millbase is then subjected to liquefaction and saccharification. Since this millbase naturally comprises, besides starch, a series of nonstarchy constituents which may adversely affect the fermentation, these constituents are usually removed prior to fermentation. The removal can be effected either directly after grinding (WO 02/077252; JP 2001-072701; JP 56-169594; CN 1218111), after liquefaction (WO 02/077252; CN 1173541) or subsequently to saccharification (CN 1266102; Beukema et al.: Production of fermentation syrups by enzymatic hydrolysis of potatoes; potato saccharification to give culture medium (Conference Abstract), Symp. Biotechnol. Res. Neth. (1983), 6; NL8302229). However, all variants involve the use of a substantially pure starch hydrolyzate in the fermentation.

More recent processes for fermentative production of organic compounds comprise in particular a purification of the starch feedstocks prior to fermentation, for example the purification of liquefied and saccharified starch solutions (JP 57159500), or provide methods which are intended to make possible the preparation of fermentation media from renewable resources (EP 1205557).

Unprocessed starch feedstocks, in contrast, are known to be employed on a large scale in the fermentative production of bioethanol. Here, the starch feedstocks, usually whole cereal grains, are first subjected to dry milling, and the starch constituent of the starch feedstock is subsequently hydrolyzed using enzymes. Here, the hydrolysis can be carried out batchwise, for example in stirred vessels, or else continuously, for example in jet cookers. Descriptions of suitable processes can be found for example in "The Alcohol Textbook—A reference for the beverage, fuel and industrial alcohol industries", Jaques et al. (Ed.), Nottingham Univ. Press 1995, ISBN 1-8977676-735, Chapter 2, pp. 7 to 23, and in McAloon et al., "Determining the cost of producing ethanol from corn starch and lignocellulosic feedstocks", NREL/TP-580-28893, National Renewable Energy Laboratory, October 2000.

Since in the fermentative production of bioethanol the product of value is obtained by distillation, the use of starch feedstocks from the dry-milling process in non-pre-purified form does not constitute a serious problem. However, when using a dry-milling method for the production of other microbial metabolites, the solids stream which is introduced into the fermentation via the sugar solution is problematic since it not only may have an adverse effect on the fermentation, for example regarding the oxygen transfer rate or the oxygen requirement of the microorganisms employed (cf., in this context, Mersmann, A. et al.: Selection and Design of Aerobic Bioreactors, Chem. Eng. Technol. 13 (1990), 357-370), but may also considerably complicate the subsequent workup.

Moreover, as a result of the introduction of solids, the viscosity of the suspension may reach a critical value even whilst the starch-containing suspension is being prepared, as a result of which for example a suspension containing more than 30% by weight of corn meal is no longer homogenously miscible in water (Industrial Enzymology, 2nd Ed., T. Godfrey, S. West, 1996). This limits the glucose concentration in traditional procedures. With regard to the fermentative production of bioethanol, this is no longer relevant in as far as higher concentrations could in any case not be converted in a sensible manner as a result of the toxicity of the product to the yeasts employed for the fermentation.

Feeding to the fermentation sugar-containing media with a low sugar concentration is in principle disadvantageous in the fermentative production of organic metabolites other than ethanol because this procedure results in a disproportionate dilution of the fermentation liquor and, as a consequence, the achievable final concentration of the products of interest is reduced which firstly results in increased costs when these products are obtained from the fermentation medium and the space-time yield decreases. These considerations are of importance in particular in the case where a starch hydrolyzate which is produced for a large-volume bioethanol production and which traditionally has low sugar or glucose concentrations of up to approximately 30 or 33% by weight is intended to be fed in part to a lower-volume secondary fermentation for the production of other chemicals.

On the other hand, higher concentrations of metabolizable monosaccharides in the fermentation medium may result in inhibition of the fermentation or of the growth of the microorganism, or lead to metabolic changes of the microorganisms employed. In *E. coli*, for example, an unduly high concentration of free glucose results in the formation of organic acids (acetate), while *Saccharomyces cerevisae*, for example, switches to fermentation in such a case, even though sufficient oxygen is present in aerated fermenters (crabtree effect). Higher concentrations of metabolizable monosaccharides in the sugar-containing media fed into the fermentation can therefore have an advantageous effect on the fermentation during the feeding phase. The use of higher-concentrated media in the batch phase, i.e. during the growth phase of the microorganisms in the fermentation batch, before further sugars are fed into the fermentation by the feed stream, is also problematic since many strains require glucose concentrations of below 6% by weight for their growth.

Owing to these difficulties and limitations, dry-milling methods as they have been employed widely for the production of bioethanol have as yet remained without particular economical importance in the fermentative production of microbial metabolites other than ethanol.

To date, attempts to apply the dry-milling concept and the advantages which exist in principle in connection with this method, to the industrial-scale production of microbial metabolites have only been described using cassava as starch feedstock. Thus, JP 2001/275693 describes a method for the fermentative production of amino acids in which peeled cassava tubers which have been ground in the dry state are employed as starch feedstock. It is necessary, in order to carry out the process, to adjust the particle size of the millbase to ≤150 μm. In the filtration step which is employed for this purpose, part of the millbase used, including non-starch-containing constituents, are removed before the starch obtained is liquefied/saccharified and subsequently fermented. In this process, moderate sugar concentrations are obtained. A similar process is described in JP 2001/309751 for the production of an amino-acid-containing feed additive.

Increased sugar concentrations in the liquid medium employed for the fermentation can be achieved by using a millbase, for the saccharification, which largely comprises the solid, nonstarchy constituents of the starch feedstock, by the process described in WO 2005/116228 (PCT/EP2005/005728) of the applicant company. Surprisingly, it has emerged that the solid, nonstarchy constituents which are present in the starch feedstock need not be removed before the fermentation. The process described can be carried out during in-situ saccharification of the liquefied starch feedstock. A similar process using starch feedstock selected among cereal grains is described in PCT/EP2006/066057 (the earlier patent application DE 102005042541.0) of the applicant company.

It is an object of the present invention to provide another process for the fermentative production of organic compounds which requires no, at least no complete, previous removal of the nonstarchy solid constituents present in the starch feedstock. In particular, the process should require relatively uncomplicated equipment and make possible the use of media with a high sugar concentration. Moreover, it was to be distinguished by easy handling of the media used and by their unproblematic use in the fermentation process. In particular, the process was to allow the use of cereals as starch feedstock.

Surprisingly, we have found that a fermentative process for the production of organic compounds despite the inherently high introduction of solids can be carried out in an efficient manner by preparing a dextrin-containing medium (1) by milling and liquefying starch feedstock without previously removing all of the nonstarchy solid constituents of the starch feedstock and employing this dextrin-containing medium in a fermentation without the addition of saccharifying enzymes.

The invention thus relates to a process for the production of at least one organic compound having at least 3 C atoms or having at least 2 C atoms and at least 1 N atom by means of fermentation, comprising the following steps:

a1) milling a starch feedstock, thus obtaining a millbase which comprises at least part of the nonstarchy solid constituents of the starch feedstock;

a2) suspending the millbase in an aqueous liquid and liquefying the millbase present in the aqueous liquid in the presence of at least one starch-liquefying enzyme, obtaining an aqueous dextrin-containing medium (1) which comprises at least a part of the nonstarchy solid constituents of the starch feedstock; and b) using the aqueous dextrin-containing medium (1) in a fermentation for culturing a microorganism which is capable of overproducing the organic compound;

enzymes which hydrolyze the dextrins to monosaccharides being added in an amount of less than 0.001% by weight based on the total weight of the starch feedstock employed, or not at all.

Despite the content of solid, nonstarchy constituents of the starch feedstock employed in the dextrin-containing medium (1), the fermentative process according to the invention can be carried out in an efficient manner without requiring the addition of saccharifying enzymes. However, small amounts which are not sufficient for carrying out a complete saccharification, typically less than 0.001% by weight, in particular less than 0.0005% by weight, based on the total weight of the starch feedstock employed, may be added.

As a result of the use of dextrins for culturing the microorganisms, a high concentration of metabolizable sugars in the fermentation medium, both in the batch phase and in the feed phase, may be established without this resulting in undesirable secondary reactions, so that an undesirable dilution of the fermentation liquor is avoided. Moreover, viscosity problems as can arise during the liquefaction of the starch feedstock at higher concentrations of millbase are avoided largely by the process according to the invention.

Here and hereinbelow, the terms "dextrin-containing medium" and "dextrin-containing liquid" are used synonymously. The skilled worker will recognize that the microorganism employed in the fermentation must be capable of metabolizing the dextrins present in the aqueous dextrin-containing medium without it being necessary for the former to be hydrolyzed to di- and/or monosaccharides by the external addition of saccharifying enzymes. The dextrins are metabolized by the microorganism, probably after having been hydrolyzed by saccharifying enzymes which are inherent to the strain, for example glucoamylases which are inherent to the strain. A particularly advantageous aspect of the process according to the invention is in the latter case that the saccharification rate during the fermentation, in particular the liberation of glucose, is adapted automatically to the requirement of the microorganisms, firstly by the amount of biomass and secondly by the expression level of the saccharifying enzymes which are inherent to the strain.

Here and hereinbelow, the term "liquefaction" means the hydrolytic degradation of starch to oligosaccharides, in particular dextrins.

Here and hereinbelow, the terms "saccharification" or "to saccharify" mean the hydrolysis of dextrins to monosaccharides, in particular to monosaccharides such as glucose. Accordingly, a "saccharifying enzyme" is understood as meaning an enzyme which hydrolyzes dextrins to monosaccharides.

Here and hereinbelow, the term "dextrin" is understood as meaning oligosaccharides which are obtained as a result of the hydrolytic degradation of starch and which, as a rule, consist of 3 to 18, in particular 6 to 12, monosaccharide units, in particular of glucose units.

The terms "content of glucose equivalents" and "sugar concentration" refer to the total concentration of mono-, di- and oligosaccharides in the medium which is potentially available for a fermentation. The term "glucose equivalents" also comprises the metabolizable sugars or sugar units which are other than glucose.

Here and hereinbelow, the terms "overproducing" or "overproduction" are used when referring to a microorganism to characterize the characteristic of the latter of producing one or more of its metabolites in an amount which exceeds the amount required for the multiplication of the microorganism, resulting in the accumulation in the fermentation medium, which accumulation can take place in an extracellular or intracellular fashion.

Suitable as starch feedstock for the process according to the invention are, mainly, dry cereals or seeds where the starch amounts to at least 40% by weight and preferably at least 50% by weight in the dried state. They are found in many of the cereal plants which are currently grown on a large scale, such as maize, wheat, oats, barley, rye, triticale, rice, and in sugar beet, potatoes, cassava and various sorghum and millet species, for example sorgo and milo. The starch feedstock is preferably selected from among cereal, especially among maize, rye, triticale and wheat kernels. In principle, the process according to the invention can also be carried out with similar starch feedstocks such as, for example, a mixture of various starch-containing cereals or seeds.

To prepare the dextrin-containing liquid the starch feedstock in question is milled in step a1), with or without addition of liquid, for example water, preferably without addition of liquid. It is also possible to combine dry milling with a subsequent wet-milling step.

Apparatuses which are typically employed for dry milling are hammer mills, rotor mills or roller mills; those which are suitable for wet grinding are paddle mixers, agitated ball mills, circulation mills, disk mills, annular chamber mills, oscillatory mills or planetary mills. In principle, other mills are also suitable. The amount of liquid required for wet grinding can be determined by the skilled worker in routine experiments. It is usually adjusted in such a way that the dry matter content is in the range of from 10 to 20% by weight.

Milling brings about a particle size which is suitable for the subsequent process steps. In this context, it has proved advantageous when the millbase obtained in the milling step, in particular the dry milling step, in step a1) has flour particles, i.e. particulate constituents, with a particle size in the range of from 100 to 630 µm in an amount of from 30 to 100% by weight, preferably 40 to 95% by weight and especially preferably 50 to 90% by weight. Preferably, the millbase obtained comprises 50% by weight of flour particles with a particle size of more than 100 µm. As a rule, at least 95% by weight of the ground flour particles have a particle size of less than 2 mm. In this context, the particle size is measured by means of screen analysis using a vibration analyzer. In principle, a small particle size is advantageous for obtaining a high product yield. However, an unduly small particle size may result in problems, in particular problems due to clump formation/agglomeration, when the millbase is slurried during liquefaction or processing, for example during drying of the solids after the fermentation step.

Usually, flours are characterized by the extraction rate or by the flour grade, whose correlation with one another is such that the characteristic of the flour grade increases with increasing extraction rate. The extraction rate corresponds to the amount by weight of the flour obtained based on 100 parts by weight of millbase employed. While, during the milling process, pure, ultrafine flour, for example from the interior of the cereal kernel, is initially obtained, with further milling, i.e. with increasing extraction rate, the amount of crude fiber and husk content in the flour increases and the starch content decreases. The extraction rate is therefore also reflected in what is known as the flour grade, which is used as a figure for classifying flours, in particular cereal flours, and which is based on the ash content of the flour (known as ash scale). The flour grade or type number indicates the amount of ash (minerals) in mg which is left behind when 100 g of flour solids are incinerated. In the case of cereal flours, a higher type number means a higher extraction rate since the core of the cereal kernel comprises approximately 0.4% by weight of ash, while the husk comprises approximately 5% by weight of ash. In the case of a lower extraction rate, the cereal flours thus consist predominantly of the comminuted endosperm, i.e. the starch content of the cereal kernels; in the case of a higher extraction rate, the cereal flours also comprise the comminuted, protein-containing aleurone layer of the grains; in the case of coarse meal, they also comprise the constituents of the protein-containing and fat-containing embryo and of the seed husks, which comprise raw fiber and ash. For the purposes of the invention, flours with a high extraction rate, or a high type number, are preferred in principle. If cereal is employed as starch feedstock, it is preferred that the intact kernels together with their husks are milled and further processed, if appropriate after prior mechanical removal of the embryo and the husks beforehand.

In accordance with the invention, the millbase used comprises at least some, preferably at least 20% by weight, in particular at least 50% by weight, specifically at least 90% by weight and very specifically at least 99% by weight of the nonstarchy solid constituents which are present in the milled cereal kernels, corresponding to the extraction rate. Based on the starchy constituents of the millbase (and thus on the amount of metabolizable sugar in the dextrin-containing medium (1)), the nonstarchy solid constituents in the millbase preferably amount to at least 10% by weight and in particular at least 15% by weight, for example from 15 to 75% by weight and specifically in the range of from 20 to 60% by weight.

The millbase intended for liquefaction in step a2) is mixed in accordance with the invention with an aqueous liquid, for example fresh water, recirculated process water, for example from a subsequent fermentation, or with a mixture of these liquids. As a rule, this will give rise to an aqueous suspension. As a rule, such an amount of starch feedstock or millbase will be mixed with the aqueous liquid and liquefied in the latter that a concentration of glucose equivalents of at least 40% by weight, based on the total weight of the medium (1), is present in the aqueous dextrin-containing liquid (1). The dry-matter content in the resulting medium (1) is typically at least 50% by weight based on the total weight of the medium (1).

To carry out the process according to the invention, the aqueous liquid used for suspending the solid millbase may be prewarmed to a moderately elevated temperature, for example in the range of from 40 to 60° C. However, it is preferred to employ the liquids at room temperature.

To carry out the liquefaction of the starch portion of the millbase in accordance with step a2), it has proved advantageous before the beginning of the liquefaction only to mix a part of the entire millbase with the aqueous liquid and to add the remainder of the millbase later to the aqueous liquid during the liquefaction process, either continuously or batchwise.

The liquefaction of the millbase in accordance with step a2) can be effected by customary processes with which the skilled worker is familiar, for example by the methods described in "The Alcohol Textbook—A reference for the beverage, fuel and industrial alcohol industries", which has been described at the outset, Chapter 2, pp. 7 to 23.

In accordance with the invention, the liquefaction process in step a2) is carried out in the presence of at least one starch-liquefying enzyme. To this end, it is possible, in principle, to employ all starch-liquefying enzymes, in particular α-amylases (enzyme class EC 3.2.1.1), for example α-amylases which have been obtained from *Bacillus lichenformis* or *Bacillus staerothermophilus*, specifically those which are used for liquefying materials, obtained by dry-milling methods, for the purposes of bioethanol production. The α-amylases which are suitable for liquefaction are also commercially available, for example from Novozymes under the name Termamyl 120 L, type L; or from Genencor under the name Spezyme. A combination of different α-amylases may also be employed for the liquefaction.

This gives an aqueous liquid which comprises the liquefied starch portion from the millbase, typically dextrins with, as a rule, 3 to 18, in particular 6 to 12, monosaccharide units, if appropriate further oligosaccharides, if appropriate small amounts of mono- and/or disaccharides (as a rule <30% by weight, frequently <25% by weight, <20% by weight, in particular <10% by weight, based on the total amount of mono-, di- and oligosaccharides) and the nonstarchy constituents of the millbase employed, in particular the solid, nonstarchy constituents of the millbase employed for the liquefaction.

The amounts of starch-liquefying enzyme and millbase will advantageously be chosen in such a way that the viscosity during the gelling process is sufficiently reduced to make possible an efficient mixing of the suspension, for example by means of stirring. The viscosity of the reaction mixture during the gelling process is preferably not more than 20 Pas, more preferably not more than 15 Pas and most preferably not more than 8 Pas. As a rule, the viscosity is measured using a Haake viscometer type Roto Visko RV20 equipped with an M5 measuring system and an MVDIN instrumentation, at a temperature of 50° C. and a shear rate of 200 s$^{-1}$.

The α-amylase (or the starch-liquefying enzyme used) can initially be introduced into the reaction vessel or else added during step a2). Preferably, a part of the α-amylase required in step a2) is added at the beginning of step a2), or this part is initially introduced into the reactor. The total amount of α-amylase is usually in the range of from 0.002 to 3.0% by weight, preferably of from 0.01 to 1.5% by weight and especially preferably from 0.02 to 0.5% by weight, based on the total amount of starch feedstock employed.

The liquefaction can be carried out above or below the gelling temperature. Preferably, the liquefaction in step a2) is carried out at least in part above the gelling temperature, or gelatinization temperature, of the starch employed (known as the cooking process). The temperature required for the starch in question is known to the skilled worker (see "The Alcohol Textbook—A reference for the beverage, fuel and industrial alcohol industries", which has been cited at the outset, Chapter 2, p. 11) or can be determined by him by routine experimentation. As a rule, the temperature chosen is in the range of between 80 and 165° C., preferably between 90 and 150° C. and especially preferably in the range of from 100 to 140° C., the temperature, as a rule, being at least 5 K, preferably at least 10 K and especially preferably at least 20 K, for example 10 to 100 K, in particular 20 to 80 K, above the gelling temperature. At these temperatures, the granular structure of the starch is destroyed (gelling), making the enzymatic degradation of the latter possible.

For α-amylase (or the starch-liquefying enzyme used) to be optimally effective, step a2) is preferably carried out at least for some time at the pH optimum of the liquefying enzyme, frequently at a pH in the weakly acidic range, preferably between 4.0 and 7.0, more preferably between 5.0 to 6.5, the pH adjustment usually being carried out before or at the beginning of step a2); it is preferred to check and, if appropriate, readjust this pH during the liquefaction process. The pH is preferably adjusted using dilute mineral acids such as $H_2SO_4$ or $H_3PO_4$ or dilute aqueous alkali hydroxide solutions such as NaOH or KOH.

In a preferred embodiment for liquefying the starch portion in the millbase in step a2), at least some of the millbase is added continuously or batchwise to the aqueous liquid. Preferably, at least 40% by weight, in particular at least 50% by weight and very especially preferably at least 55% by weight are added during the course of the liquefaction process to the reactor. Frequently, the added amount will not exceed 90% by weight, in particular 85% by weight and especially preferably 80% by weight. Preferably, the portion of millbase which is added in the course of the process is fed into the reactor under conditions as are prevailing during the liquefaction phase. The addition can be effected batchwise, i.e. portionwise, in several portions, which amount to preferably in each case not more than 30% by weight, especially preferably not more than 20% by weight, for example 1 to 30% by weight and in particular 2 to 20% by weight of the total amount of the millbase to be liquefied, or else continuously. An essential aspect of this embodiment is that only some of the millbase, preferably not more than 60% by weight, in particular not more than 50% by weight and especially preferably not more than 45% by weight of the millbase is present in the reactor at the beginning of the liquefaction, while the remainder of the millbase is added during the liquefaction phase.

The liquefaction can also be carried out continuously, for example in a multi-step reaction cascade.

In a preferred embodiment, step a2) of the process according to the invention is carried out in such a way that a portion amounting to not more than 60% by weight, preferably not more than 50% by weight and especially preferably not more than 45% by weight, for example 10 to 60% by weight, in particular 15 to 50% by weight, and especially preferably 20 to 45% by weight, based on the total amount of millbase, is initially suspended in the aqueous liquid, and the liquefaction is subsequently carried out.

In a preferred embodiment, the discontinuous or continuous addition, in particular the portionwise addition, of some of the millbase in the presence of the at least one α-amylase is carried out in such a way that the viscosity of the liquid medium is not more than 20 Pas, preferably not more than 15 Pas and especially preferably not more than 8 Pas. To aid the control of the viscosity, it has proved advantageous to add at least 25% by weight, preferably at least 35% by weight and especially preferably at least 50% by weight of the total amount of the added millbase at a temperature above the gelatinization temperature of the starch present in the millbase. Moreover, controlling the viscosity can furthermore be influenced by adding the at least one starch-liquefying enzyme, preferably an α-amylase, and/or the at least one saccharifying enzyme, preferably a glucoamylase, portionwise themselves.

To carry out the method according to the invention, it is possible to prewarm the aqueous liquid used for suspending the solid millbase at a moderately increased temperature, for example in the range of from 40 to 60° C. However, it is preferred to employ the liquids at room temperature.

Then, the at least one starch-liquefying enzyme, preferably an α-amylase, is added to this suspension of the millbase. If some of the millbase is added only during the liquefaction phase, it is advantageous at the beginning only to add some of the α-amylase, for example 10 to 70% by weight, and in particular 20 to 65% by weight, based on all of the α-amylase employed in step a2). The amount of α-amylase added at this point in time depends on the activity of the α-amylase in question under the reaction conditions with regard to the starch feedstock used and is generally in the range of from 0.0004 to 2.0% by weight, preferably from 0.001 to 1.0% by weight and especially preferably from 0.02 to 0.3% by weight, based on the total amount of the starch feedstock employed. As an alternative, the α-amylase portion can be mixed with the liquid used before the suspension is made.

The amount or portion of α-amylase employed is preferably added to the suspension before heating to the temperature used for the liquefaction has started, in particular at room temperature or only moderately increased temperature, for example in the range of from 20 to 30° C.

The suspension thus made is then heated, preferably to a temperature above the gelling temperature of the starch used. As a rule, a temperature in the range of between 80 and 165° C., preferably between 90 and 150° C. and especially preferably between 100 and 140° C. is chosen, the temperature usually preferably being at least 5 K, preferably at least 10 K and especially preferably at least 20 K, for example 10 to 100 K, in particular 20 to 80 K above the gelling temperature. While monitoring the viscosity, further portions of the starch feedstock, for example in each case 1 to 30% by weight and in particular from 2 to 20% by weight, based on all of the millbase employed, are added if appropriate gradually to the starch-containing suspension. It is preferred in this case to add the portion of the millbase to be added in the course of the liquefaction step in at least 2, preferably at least 4 and especially preferably at least 6 fractions to the reaction mixture. As an alternative, the portion of the millbase which has not been employed for making the suspension can be added continuously during the liquefaction step in this embodiment. During the addition, the temperature should advantageously be kept above the gelling temperature of the starch.

After the desired temperature has been reached, or, if appropriate, after all of the flour has been added, the reaction mixture is usually maintained for some time, for example for 10 to 60 minutes or longer, if required, at the temperature set above the gelling temperature of the starch, i.e. cooked. Then, as a rule, the reaction mixture is cooled to a somewhat lower temperature, but preferably above the gelling temperature, for example to 70 to 90° C. Thereafter, if appropriate, a further portion of α-amylase, preferably the largest portion, is added. In this case, the amount of α-amylase added at this point in time is, depending on the activity under the reaction conditions of the α-amylase used, preferably from 0.002 to 2.0% by weight, especially preferably from 0.01 to 1.0% by weight and very especially preferably from 0.02 to 0.4% by weight, based on the total amount of the starch feedstock employed.

To fully degrade the starch into dextrins, the reaction mixture is held at the set temperature, or, if appropriate, heated further, until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

Alternatively, it is possible, to liquefy the starch portion, first to heat the aqueous suspension comprising the millbase to a temperature above the gelatinization temperature of the starch present in the starch feedstock or the millbase by means of introducing steam. Typically, the suspension will be heated at a temperature which is at least 10 K and in particular at least 20 K, for example 10 to 100 K, in particular 20 to 80 K, above the gelatinization temperature in question. In particular, the suspension is heated to temperatures in the range of from 90 to 150° C., specifically in the range of from 100 to 140° C.

The steam employed for heating the suspension is typically superheated steam with a temperature of at least 105° C., in particular at least 110° C., for example 110 to 210° C. The steam is preferably introduced into the suspension at superatmospheric pressure. Accordingly, the steam preferably has a pressure of at least 1.5 bar, for example 1.5 to 16 bar, in particular 2 to 12 bar.

As a rule, steam is introduced into the suspension in such a way that the steam is introduced into the suspension at superatmospheric pressure, preferably a superatmospheric pressure of 1 to 10 or 11 bar, in particular 1.5 to 5 bar, preferably at high speed. The result of introducing the steam is that the suspension is instantly heated to temperatures of above 90° C., that is temperatures above the gelatinization temperature.

Heating with steam is preferably carried out in a continuously operating device which is charged with the suspension continuously at a specific feed pressure which is the result of the viscosity of the suspension, the feed rate and the geometry of the device and which, in the suspension charge zone, is charged with the hot steam via an adjustable nozzle at elevated pressure based on the feed pressure. Feeding the steam at elevated pressure means that not only is the suspension heated, but also mechanical energy is introduced into the system, and this mechanical energy promotes a further comminution of the millbase particles, brings about a particularly uniform energy supply, and thus brings about especially uniform gelatinization of the granular starch particles in the millbase. These devices typically have a tubular geometry. The steam is preferably fed in along the longitudinal axis of the tubular device. As a rule, the suspension is supplied at an angle of at least 45° or at a right angle. The adjustable area nozzle typically has a conical geometry which tapers in the flow direction of the steam. A needle, or a nappe which is arranged on a longitudinally displaceable rod, is arranged within this nozzle. Needle, or nappe, together with the cone of the nozzle, form an aperture. By displacing the needle, or the rod, longitudinally, the size of the aperture, and thus the cross-sectional area of the nozzle port can be adjusted in a simple manner, whereby the speed at which steam is supplied can be controlled in a simple manner.

These devices are typically also equipped with a mixing tube into which the suspension is transported after the steam has been supplied and in which the suspension leaves the device. This mixing tube is usually arranged along the steam supply and perpendicular to the feed. The mixing tube and the nozzle together typically form an aperture through which the suspension is transported. As a result of this aperture, additional shear forces act on the suspension during the transport process and thus increase the supply of mechanical energy to the suspension. The mixing tube can be arranged in such a way that it is longitudinally displaceable. Displacing the mixing tube is a simple way of adjusting the size of the aperture and thus of the pressure drop in the device.

Such devices are known from the prior art under the name jet cooker, for example the device which is shown in "The Alcohol Textbook", Chapter 2, loc. cit., FIG. 13, and commercially available, for example under the name HYDRO-HEATER® from Hydro Thermal Corp. Waukesha Wis., USA.

When reaction is carried out continuously, the suspension treated with steam is, as a rule, subsequently transferred into an after-reaction zone in order to continue the gelling of the starch constituents. Typically, a superatmospheric pressure, typically an absolute pressure of in the range of from 2 to 8 bar, prevails in the after-reaction zone. The temperatures in the after-reaction zone are typically in the range of from 90 to 150° C. The residence time in this after-reaction zone can be in the range of from 1 minute to 4 hours, depending on the temperature of the suspension. The after-reaction zones typically have a tubular or column geometry. In one embodiment, the after-reaction zone has the geometry of a vertically arranged column. Here, the suspension, once it has left the steam treatment device, is applied in the upper zone of the column and withdrawn in the lower zone. In another embodiment of the invention, the after-reaction zone has a tubular geometry.

After the suspension has left the after-reaction zone, the pressure is released, as a rule, and a liquefaction is subsequently carried out. Releasing the pressure is preferably carried out in the form of a flash evaporation in order to cool the suspension to, preferably, temperatures of below 100° C., in particular below 85° C. As a rule, the starch thus disintegrated is then liquefied in a separate reaction vessel. The liquefaction can be carried out as described above.

In a preferred embodiment of the invention, at least some or all, generally at least 50%, in particular at least 80%, or else all of the starch-liquefying enzyme is added to the suspension of the millbase in the aqueous liquid before the steam heating process. In this manner, the liquefaction process already takes place while the mixture is heated to temperatures of above the gelatinization temperature. Heating with steam, and the after-reaction phase, are carried out appropriately. A subsequent liquefaction step in a separate reaction vessel can be dispensed with. However, such a liquefaction step will preferably be carried out to complete the degradation of the starch into dextrins.

To stabilize the enzymes employed, the concentration of $Ca^{2+}$ ions may, if appropriate, be adjusted to an enzyme-specific optimum value, for example using $CaCl_2$. Suitable concentration values can be determined by the skilled worker in routine experiments. If, for example Termamyl is employed as α-amylase, it is advantageous to adjust the $Ca^{2+}$ concentration to, for example, 10 to 100 ppm, preferably 20 to 80 ppm and especially preferably approximately 30 to 70 ppm in the liquid medium, the unit ppm being based on weight and meaning g/1000 kg.

To fully degrade the starch into dextrins, the reaction mixture is held at the set temperature until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

Since, as a rule, millbase which comprises essentially all or virtually all of the constituents of the starch feedstock or, besides the starch, also a portion of the solid nonstarchy constituents is employed for the preparation of the dextrin-containing liquid (1) (i.e. the nonstarchy solid constituents of the starch feedstock are not fully removed), the dextrin-containing liquid (1) obtained also comprises some or all of the nonstarchy solid constituents of the starch feedstock. This frequently brings about the introduction of an amount of phytate, for example from the cereal, which amount is not to be overlooked. To avoid the inhibitory effect which thus results, it is advantageous to add, in step a2), at least one phytase to the medium (1) before subjecting the medium to a fermentation step. The phytase can be added before, during or after the liquefaction, if it is sufficiently stable to the respective high temperatures. Any phytases can be employed as long as their activity is in each case not more than marginally affected under the reaction conditions. Phytases used preferably have a heat stability (T50)>50° C. and especially preferably >60° C. The amount of phytase is usually from 1 to 10 000 units/kg starch feedstock and in particular 10 to 4000 units/kg starch feedstock.

It has proved advantageous during the preparation of the dextrin-containing liquid (1) also to add further enzymes, for example pullulanases, cellulases, hemicellulases, glucanases, xylanases or proteases. The addition of these enzymes can have a positive effect on the viscosity, i.e. reduce the viscosity (for example by cleaving long-chain (also termed longer-chain) glucans and/or (arabino-)xylanes), and bring about the liberation of metabolizable glucosides and the liberation of (residual) starch. The use of proteases has analogous positive effects, it additionally being possible to liberate amino acids which act as growth factors for the fermentation.

The dextrin-containing liquid (1) obtained in step a2) has, as a rule, a concentration of glucose equivalents of at least 20% by weight (=200 g/kg), in particular at least 40% by weight and specifically at least 50% by weight, frequently in the range of from 30 to 75% by weight, preferably in the range of from 40 to 70% by weight, in particular in the range of from 50 to 65% by weight, in each case based on the total weight of the medium (1).

The dry-matter content in the resulting liquid (1) is typically at least 25% by weight, preferably at least 40% by weight, in particular at least 50% by weight, specifically at least 60% by weight, and will, as a rule, not exceed 80% by weight, in each case based on the total weight of the medium (1).

The glucose equivalents present in the resulting dextrin-containing liquid (1) are essentially present in the form of oligosaccharides, in particular dextrins. The main constituent of these oligosaccharides, or dextrins, is typically glucose, it also being possible for the medium to comprise small amounts of mono- and/or disaccharides and oligosaccharide units consisting of other monosaccharide units. The sugar-containing constituents in the dextrin-containing medium (1), i.e. the mono-, di- and oligosaccharides, typically comprise at least 70% by weight, frequently at least 75% by weight, in particular at least 80% by weight, specifically at least 90% by weight of oligosaccharides, in particular dextrins, i.e. the mono- and disaccharides amount to less than 30% by weight, frequently less than 25% by weight, in particular less than 20% by weight and specifically less than 10% by weight.

The glucose which is present in free or bound form usually amounts to in the range of from 50 to 99% by weight, in particular from 75 to 97% by weight and specifically from 80 to 95% by weight of the glucose equivalents of the medium (1), based on the total amount of glucose equivalents.

The aqueous dextrin-containing liquid (1) which has been obtained in step a2) is used in accordance with the invention in step b) for the fermentative production of the desired organic compound. To this end, the dextrin-containing liquid (1) is fed into a fermentation, where it serves for culturing the microorganisms employed in the fermentation. The organic compound in question is here obtained as a volatile or non-volatile microbial metabolite.

As a rule, the resulting aqueous dextrin-containing liquid (1) is employed directly in a fermentation in accordance with step b), without a separate saccharification tank. As a rule, the dextrin-containing liquid (1) will be cooled to the fermentation temperature, usually in the range of from 32 to 37° C., before being fed into the fermentation.

Before the fermentation, the aqueous dextrin-containing liquid (1) can, if appropriate, be sterilized, the microorganisms usually being destroyed by thermal or chemical processes. For example, the aqueous dextrin-containing liquid (1) is heated to temperatures of usually above 80° C. for this purpose. The destruction, or lysis, of the cells can take place directly before the fermentation. To this end, all of the dextrin-containing liquid (1) is subjected to a lytic, or destruction, step. This can be carried out thermally, mechanically or chemically. However, for the purposes of the process according to the invention, it has not proved necessary to precede the fermentation by a sterilization step as described herein; rather, it has proved advantageous not to carry out such a sterilization step. Accordingly, a preferred embodiment of the invention relates to a process in which the medium (1) which is obtained in step a2) is fed directly into the fermentation, i.e. before previously being sterilized.

During the fermentation, the metabolization of the dextrins takes place in accordance with the invention essentially without the addition of saccharifying enzymes. Here, the dextrins are metabolized by the microorganism, probably after having been hydrolyzed by strain-inherent saccharifying enzymes, for example strain-inherent glucoamylases. The liquefied starch constituents are probably saccharified in parallel with the metabolization of the sugar, in particular of the monosaccharide glucose, by the microorganisms.

In a preferred embodiment, the microorganism employed for the fermentation is therefore selected among microorganisms which express, or produce, enzymes which hydrolyze dextrins to monosaccharides, in particular among those which produce, or express, glucoamylases. Such microorganisms are known to the skilled worker or can be determined by routine experiments, for example by screening methods, for example by a screening for glucoamylase, for example by growing the microorganism in a shake-flask test followed by assaying the enzyme activity for glucoamylase, or by screening with the aid of primers/probes using the screening methods described in the examples section, and via database researchers in enzyme databases such as Brenda [Schomburg I., Chang A., Hofmann O., Ebeling C., Ehrentreich F., Schomburg D. BRENDA: a resource for enzyme data and metabolic information. Trends Biochem Sci. 2002 January; 27(1):54-6.], Swissprot [Boeckmann B., Bairoch A., Apweiler R., Blatter M.-C., Estreicher A., Gasteiger E., Martin M. J., Michoud K., O'Donovan C., Phan I., Pilbout S., Schneider M. The *SWISS-PROT protein knowledgebase and its supplement TrEMBL in* 2003 Nucleic Acids Res. 31:365-370 (2003)], ERGO-WIT [Overbeek R, Larsen N, Walunas T, D'Souza M, Pusch G, Selkov E Jr, Liolios K, Joukov V, Kaznadzey D, Anderson I, Bhattacharyya A, Burd H, Gardner W, Hanke P, Kapatral V, Mikhailova N, Vasieva O, Osterman A, Vonstein V, Fonstein M, Ivanova N, Kyrpides N. The ERGO(TM) genome analysis and discovery system. Nucleic Acids Res 2003 Jan. 1; 31 (1): 164-71; Overbeek R, Larsen N, Pusch G D, D'Souza M, Selkov E Jr, Kyrpides N, Fonstein M, Maltsev N, Selkov E. WIT: integrated system for high-throughput genome sequence analysis and metabolic reconstruction. Nucleic Acids Research, 2000; Vol. 28, No. 1: 123-125], CAZY [Coutinho, P. M. & Henrissat, B. (1999) Carbohydrate-Active Enzymes server at URL: http://afmb.cnrs-mrs.fr/CAZY/; Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12] and PIR [Cathy H. Wu, Lai-Su L. Yeh, Hongzhan Huang, Leslie Arminski, Jorge Castro-Alvear, Yongxing Chen, Zhang-Zhi Hu, Robert S. Ledley, Panagiotis Kourtesis, Baris E. Suzek, C. R. Vinayaka, Jian Zhang, and Winona C. Barker. The Protein Information Resource. Nucleic Acids Research, 31: 345-347, 2003.]

following the method described in the examples section.

Examples of suitable microorganisms with glucoamylase activity are *Agrobacterium tumefaciens, Arxula adeninivorans, Ashbya gossypii, Aspergillus awamori, Aspergillus candidus, Aspergillus foetidus, Aspergillus fumigatus, Aspergillus kawachi, Aspergillus nidulans, Aspergillus niger, Aspergillus oryzae, Aspergillus phoenicis, Aspergillus saitoi, Aspergillus shirousami, Aspergillus terreus, Athelia rolfsii, Bacillus circulans, Bacillus stearothermophilus, Beta vulgaris, Bradyrhizobium japonicum, Burkholderia cenocepacia, Burkholderia fungorum, Burkholderia pseudomallei, Candida albicans, Candida antarctica, Candida glabrata, Candida tsukubaensis, Caulobacter crescentus, Cephalosporium charticola, Cephalosporium eichhorniae Ceratocystis paradoxa, Chaetomium thermophilum, Chlorobium tepidum, Chromobacterium violaceum, Cladosporium resinae, Clostridium* sp., *Clostridium thermocellum, Clostridium thermosaccharolyticum, Coniophora puteana, Corticium rolfsii, Corynebacterium glutamicum, Cryptococcus neoformans, Debaryomyces hansenii, Debaryomyces occidentalis, Emericella nidulans, Endomyces* sp., *Endomycopsis fibuligera, Fusarium venenatum, Haloarcula marismortui, Hormoconis resinae, Humicola grisea, Humicola lanuginosa, Hypocrea lixii, Kluyveromyces lactis, Lentinula edodes, Lipomyces kononenkoae, Magnaporthe grisea, Mesorhizobium loti, Methanocaldococcus jannaschii, Methanococcus jannaschii, Methanococcus maripaludis, Methanosarcina acetivorans, Methanosarcina barkeri, Methanosarcina mazei, Monascus rubiginosus, Monascus* sp., *Mucor rouxianus, Mycobacterium bovis, Mycobacterium leprae, Mycobacterium marinum, Mycobacterium tuberculosis, Myrothecium* sp., *Neurospora crassa, Nostoc punctiforme, Oryza sativa, Paecilomyces variotii, Penaeus japonicus, Penicillium chrysogenum, Penicillium oxalicum, Picrophilus torridus, Pseudomonas fluorescens, Pseudomonas putida, Pseudomonas syringae, Ralstonia eutropha, Ralstonia metallidurans, Rana japonica, Rhizobium leguminosarum, Rhizopus delemar, Rhizopus javanicus, Rhizopus niveus, Rhizopus oryzae, Rhizopus* sp., *Rhodococcus* sp., *Rhodopseudomonas palustris, Rhodospirillum rubrum, Saccharomyces cerevisiae, Saccharomyces diastaticus, Saccharomycopsis fibuligera, Saccharomycopsis fibuligera, Schizosaccharomyces pombe, Schwanniomyces occidentalis, Shewanella oneidensis, Sphingomonas aromaticivorans, Streptomyces coelicolor, Sulfolobus acidocaldarius, Sulfolobus solfataricus, Talaromyces emersonii, Termitomyces clypeatus, Thermoactinomyces vulgaris, Thermoanaerobacter tengcongensis, Thermoanaerobacterium thermosaccharolyticum, Ther-*

*moascus crustaceus, Thermomyces lanuginosus, Thermoproteus tenax, Thielavia terrestris, Trichoderma reesei* and *Trichosporon adeninovorans.*

If the microorganisms employed in the fermentation express strain-intrinsic glucoamylases, the pH of the fermentation medium can be adjusted to a value in the optimal activity range for glucoamylase, for example to a value in the range of between 3.5 and 6.0. The pH will frequently be adjusted to an optimal value for the fermentation which may be outside the abovementioned range, for example in the range of from 6.0 to 8.0. This can be altogether advantageous for the fermentation despite the limited activity of a number of glucoamylases in this pH range or else required as a result of the fermentation conditions to be adjusted, which are to be adapted in particular to the microorganism in question. The pH range which is optimal for the fermentation can be determined by the skilled worker by routine experiments.

To obtain a high degree of conversion of the dextrins introduced into the fermentation medium via the medium (1), the fermentation medium will usually be held at the adjusted temperature over a period of, for example, 2 to 72 hours or, if appropriate, longer, for example from 2 to 96 hours, in particular from 5 to 48 hours. The monosaccharides obtained from the dextrins by hydrolysis, in particular glucose, are typically metabolized very rapidly by the microorganisms so that, as a rule, no major monosaccharide or glucose concentrations can be detected.

The fermentation can be carried out in the customary manner known to the skilled worker. To this end, the respective desired microorganism will, as a rule, be cultured in the liquid medium obtained by the method described herein.

The fermentation process can be carried out either as a batch operation or else as a fed-batch operation, (including fed batch with intermediate harvesting), the fed batch operation being preferred.

For example, the medium (1) which has been obtained by the process according to the invention, if appropriate together with a conventional sugar feedstock, i.e. metabolizable mono-, di- and/or oligosaccharides or media comprising metabolizable mono-, di- and/or oligosaccharides, if appropriate after dilution with water and addition of conventional media constituents such as buffers, nutrient salts, nitrogen feedstock such as ammonium sulfate, urea, and the like, complex nutrient media components comprising amino acids, such as yeast extracts, peptones, CSL and the like, can be inoculated with the desired microorganism and the latter can be multiplied under fermentation conditions until the microorganism concentration reaches the stationary state which is desired for the fermentation. Here, the dextrins present in the fermentation medium are metabolized and the desired metabolite is formed (also known as batch operation or batch phase).

When carrying out a fed-batch operation, the medium (1) is added continuously or batchwise to the fermentation medium after the batch phase, for example when the total sugar concentration has dropped below a specific level.

A typical embodiment of the process according to the invention is the fed-batch operation, which comprises the following steps:
b1) culturing, in an aqueous fermentation medium (2), the microorganism which is capable of overproducing the organic compound; and
b2) addition of the dextrin-containing medium (1), if appropriate together with a conventional sugar feedstock, to the fermentation medium (2), in which the dextrins present in the medium (1) are metabolized by the microorganisms which overproduce the organic compound, if appropriate after previously having been saccharified.

In step b1), for example, a traditional sugar-containing medium, usually a glucose solution, or a liquid medium (1) according to the invention, or a mixture of (1) with a conventional sugar feedstock, can first be brought to a suitable sugar concentration by dilution with an aqueous liquid, in particular water, and the media components conventionally used for fermentation purposes, such as buffers, nutrient salts, nitrogen feedstocks such as ammonium sulfate, urea and the like, complex nutrient media constituents comprising amino acids, such as yeast extracts, peptones, CSL and the like are added. Here, the ratio between the amount of sugar and liquid will, as a rule, preferably be selected in such a way that the total monosaccharide concentration in the fermentation medium (2) is less than 6% by weight, for example in the range of from ≥0 to 5% by weight, calculated as glucose equivalents and based on the total weight of the fermentation medium (2). The sugar-containing batch medium thus prepared is inocculated with the desired microorganism, and the microorganism is multiplied in the batch medium (fermentation medium (2)) under fermentation conditions until the microorganism concentration reaches a stationary state which is desired for the fermentation. During this process, the sugar provided with the fermentation medium (2) is metabolized and the desired metabolite is formed.

In the subsequent fed-batch phase, the fermentation process is maintained by addition of the dextrin-containing medium (1) to the fermentation medium (2), and the metabolite which is overproduced by the microorganism accumulates in the fermentation liquor, it being possible for the accumulation to take place in intracellular or else extracellular form. The volume ratio of added medium (1) to the batch medium provided, which comprises the microorganisms (fermentation medium (2)) is generally in the range of from approximately 1:10 to 10:1, for example in the range of from 1:5 to 5:1 and in particular in the range of from 1:1 to 5:1. The sugar concentration in the fermentation medium (2) can be controlled in particular via the feed rate of the medium (1). As a rule, the feed rate will be adjusted in such a way that the total sugar concentration, i.e. the total of oligosaccharides and monosaccharides, will not exceed a value of 30% by weight, in particular 20% by weight. The monosaccharide concentration in the fermentation liquor is preferably in the range of from >0% by weight to approximately 5% by weight and is in particular not more than 3% by weight.

In a preferred embodiment, the fermentation medium (2) in step b1) (i.e. here the batch medium) comprises essentially the dextrin-containing medium (1), the microorganisms which are capable of overproducing the organic compound, media components such as buffers, nutrient salts, nitrogen feedstocks such as ammonium sulfate, urea and the like, complex nutrient media components comprising amino acids, such as yeast extracts, peptones, CSL and the like and, if appropriate, water for dilution. To this end, a dextrin-containing medium (1) will, if appropriate, be diluted to the desired dextrin content, for example in the range of from 15 to 30% by weight, calculated as glucose equivalents and based on the total weight of the dextrin-containing medium (1), and will be used directly for making up the fermentation medium (2) (batch medium).

The dextrin content of the dextrin-containing medium in accordance with step b2) which is employed for maintaining the fermentation is usually higher, for example in the abovementioned ranges, in order to minimize the dilution of the fermentation medium (2).

Preferably, a procedure will be followed in which a dextrin-containing medium (1) with a higher dextrin content, for example with a content of at least 30% by weight, specifically at least 40% by weight and very specifically at least 50% by weight, calculated as glucose equivalents and based on the total weight of the dextrin-containing medium (1), is prepared. This medium (1) is then used firstly as described in step b1) for making up the batch medium, (fermentation medium (2)), after dilution with water and, secondly, as described in step b2) for addition to the fermentation medium (2).

Using the dextrin-containing medium (1), it is possible to produce, by way of fermentation, volatile and nonvolatile, in particular nonvolatile, microbial metabolites having at least 3 C atoms or having at least 2 C atoms and 1 N atom.

In this context, nonvolatile products are understood as meaning those compounds which cannot be recovered by distillation from the fermentation liquor without undergoing decomposition. As a rule, these compounds have a boiling point above the boiling point of water, frequently above 150° C. and in particular above 200° C. under atmospheric pressure. As a rule, they are compounds which are in the solid state under standard conditions (298 K, 101.3 kPa).

However, it is also possible to employ the aqueous dextrin-containing medium (1) in a fermentation for the production of nonvolatile microbial metabolites which, under atmospheric pressure, have a melting point below the boiling point of water and/or an oily consistency.

The term nonvolatile microbial metabolites comprises in particular organic mono-, di- and tricarboxylic acids which preferably have 3 to 10 carbon atoms and which, if appropriate, have one or more, for example 1, 2, 3 or 4, hydroxyl groups attached to them, for example tartaric acid, itaconic acid, succinic acid, propionic acid, lactic acid, 3-hydroxypropionic acid, fumaric acid, maleic acid, 2,5-furandicarboxylic acid, glutaric acid, levulic acid, gluconic acid, aconitic acid and diaminopimelic acid, citric acid; proteinogenic and non-proteinogenic amino acids, for example lysine, glutamate, methionine, phenylalanine, aspartic acid, tryptophan and threonine; purine and pyrimidine bases; nucleosides and nucleotides, for example nicotinamide adenine dinucleotide (NAD) and adenosine-5'-monophosphate (AMP); lipids; saturated and unsaturated fatty acids having preferably 10 to 22 carbon atoms, for example γ-linolenic acid, dihomo-γ-linolenic acid, arachidonic acid, eicosapentaenoic acid and docosahexaenoic acid; diols having preferably 3 to 8 carbon atoms, for example propanediol and butanediol; polyhydric (also referred to as higher-value) alcohols having 3 or more, for example 3, 4, 5 or 6, OH groups, for example glycerol, sorbitol, mannitol, xylitol and arabinitol; long-chain (also referred to as longer-chain) alcohols having at least 4 carbon atoms, for example 4 to 22 carbon atoms, for example butanol; carbohydrates, for example hyaluronic acid and trehalose; aromatic compounds, for example aromatic amines, vanillin and indigo; vitamins and provitamins, for example ascorbic acid, vitamin $B_6$, vitamin $B_{12}$ and riboflavin, cofactors and what are known as nutraceuticals; proteins, for example enzymes such as amylases, pectinases, acid, hybrid or neutral cellulases, esterases such as lipases, pancreases, proteases, xylanases and oxidoreductases such as laccase, catalase and peroxidase, glucanases, phytases; carotenoids, for example lycopene, β-carotene, astaxanthin, zeaxanthin and canthaxanthin; ketones having preferably 3 to 10 carbon atoms and, if appropriate, 1 or more hydroxyl groups, for example acetone and acetoin; lactones, for example γ-butyrolactone, cyclodextrins, biopolymers, for example polyhydroxyacetate, polyesters, for example polylactide, polysaccharides, polyisoprenoids, polyamides; and precursors and derivatives of the abovementioned compounds. Other compounds which are suitable as nonvolatile microbial metabolites are described by Gutcho in Chemicals by Fermentation, Noyes Data Corporation (1973), ISBN: 0818805086.

The term "cofactor" comprises nonproteinaceous compounds which are required for the occurrence of a normal enzyme activity. These compounds can be organic or inorganic; preferably, the cofactor molecules of the invention are organic. Examples of such molecules are NAD and nicotinamide adenine dinucleotide phosphate (NADP); the precursor of these cofactors is niacin.

The term "nutraceutical" comprises food additives which promote health in plants and animals, in particular humans. Examples of such molecules are vitamins, antioxidants and certain lipids, for example polyunsaturated fatty acids.

The metabolites produced are selected in particular among enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms and alkanediols having 3 to 10 and in particular 3 to 8 C atoms.

It is clear to the skilled worker that the compounds thus produced fermentatively are obtained in each case in the enantiomeric form produced by the microorganisms employed (if different enantiomers exist). Thus, as a rule, the respective L-enantiomer is obtained for example in the case of amino acids.

The microorganisms employed in the fermentation depend in a manner known per se on the microbial metabolites in question, as specified in detail hereinbelow. They can be of natural origin or genetically modified. Examples of suitable microorganisms and fermentation processes are those given in Table A hereinbelow:

TABLE A

| Substance | Microorganism | Reference |
|---|---|---|
| Tartaric acid | Lactobacilli, (for example Lactobacillus delbrueckii) | Rehm, H.-J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (Eds.), Genetics and Physiology of Aspergillus, London: Academic Press 1977; Miall, in Rose (Ed.), Economic Microbiology, Vol. 2, pp. 47-119, London: Academic Press 1978; U.S. Pat. No. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), Inventors: Lemme and Datta; U.S. Pat. No. 5,504,004 (1996), Inventors: Guettler, Jain and Soni; Arch. Microbiol. 167, 332-342 (1997); Guettler MV, Rumler D, Jain MK., Actinobacillus succinogenes sp. nov., a |

TABLE A-continued

| Substance | Microorganism | Reference |
|---|---|---|
| | | novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO99/06532, U.S. Pat. No. 5,869,301, U.S. Pat. No. 5,770,435 |
| Hydroxypropionic acid | Lactobacillus delbrückii, L. leichmannii or Sporolactobacillus inulinus | RÖMPP Online Version 2.2 |
| Propionic acid | Propionibacterium, for example P. arabinosum, P. schermanii, P. freudenreichii, Clostridium propionicum, | Rehm, H.-J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, for example Aspergillus flavus, A. niger, A. oryzae, Corynebacterium | U.S. Pat. No. 3,063,910 |
| Gluconic acid | Aspergilli, for example A. niger | Gutcho, Chemicals by Fermentation, Noyes Data Corporation (1973), |
| Butyric acid | Clostridium (for example Clostridium acetobutlyicum, C. butyricum) | Rehm, H.-J.: Biotechnology, Weinheim, VCH, 1980 and 1993-1995; |
| Lactic acid | Lactobacillus for example L. delbrückii, L. leichmannii, | Rehm, H.-J.: Biotechnology, Weinheim, VCH, 1980 and 1993-1995; |
| Lysine | Corynebacterium glutamicum | Ikeda, M.: Amino Acid Production Process (2003), Adv. Biochem. Engin/Biotechnol 79, 1-35. |
| Glutamate | Corynebacterium glutamicum | Ikeda, M.: Amino Acid Production Process (2003), Adv. Biochem. Engin/Biotechnol 79, 1-35. |
| Methionine | Corynebacterium glutamicum | Ikeda, M.: Amino Acid Production Process (2003), Adv. Biochem. Engin/Biotechnol 79, 1-35. |
| Phenylalanine | Corynebacterium glutamicum, E. coli | Trends Biotechnol. 3, 64-68 (1985); J. Ferment. Bio-eng. 70, 253-260 (1990). |
| Threonine | E. coli | Ikeda, M.: Amino Acid Production Process (2003), Adv. Biochem. Engin/Biotechnol 79, 1-35. |
| Aspartic acid | E. coli | Ikeda, M.: Amino Acid Production Process (2003), Adv. Biochem. Engin/Biotechnol 79, 1-35 and references cited therein, Gutcho, Chemicals by Fermentation, Noyes Data Corporation (1973) |
| Purine and pyrimidine bases | Bacillus subtilis | Rehm, H.-J.: Biotechnology, Weinheim, VCH, 1980 and 1993-1995; Gutcho, Chemicals by Fermentation, Noyes Data Corporation (1973), |
| Nicotinamide adenine dinucleotide (NAD) | Bacillus subtilis | Rehm, H.-J.: Biotechnology, Weinheim, VCH, 1980 and 1993-1995; Gutcho, Chemicals by Fermentation, Noyes Data Corporation (1973), |
| Adenosine-5'-monophosphate (AMP) | Bacillus subtilis | Rehm, H.-J.: Biotechnology, Weinheim, VCH, 1980 and 1993-1995; Gutcho, Chemicals by Fermentation, Noyes Data Corporation (1973), |
| γ-Linolenic acid | Mucor, Mortiella, Aspergillus spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Dihomo-γ-linolenic acid | Mortiella, Conidiobolus, Saprolegnia spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |

TABLE A-continued

| Substance | Microorganism | Reference |
|---|---|---|
| Arachidonic acid | Mortiella, Phytium spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Eicosapentaenoic acid | Mortiella, Phytium spp., Rhodopseudomonas, Shewanella spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Docosahexaenoic acid | Thraustochytrium, Entomophthora spp., Rhodopseudomonas, Shewanella spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Propanediol | E. coli | DE 3924423, U.S. Pat. No. 440,379, WO 9635799, U.S. Pat. No. 5,164,309 |
| Butanediol | Enterobacter aerogenes, Bacillus subtilis, Klebsiella oxytoca | Rehm, H.-J.: Biotechnology, Weinheim, VCH, 1980 and 1993-1995; Gutcho, Chemicals by Fermentation, Noyes Data Corporation (1973), H. G. SCHLEGEL and H. W. JANNASCH, 1981; Afschar et al.: Mikrobielle Produktion von 2,3-Butandiol [Microbial production of 2,3-butane diol. CIT 64 (6), 2004, 570-571 |
| Butanol | Clostridium (eg Clostridium acetobutylicum, C. propionicum) | Rehm, H.-J.: Biotechnology, Weinheim, VCH, 1980 and 1993-1995; Gutcho, Chemicals by Fermentation, Noyes Data Corporation (1973), |
| Glycerol | Yeast, Saccharomyces rouxii | Gutcho, Chemicals by Fermentation, Noyes Data Corporation (1973), |
| Mannitol | Aspergillus candida, Torulopsis mannitofaciens | Gutcho, Chemicals by Fermentation, Noyes Data Corporation (1973), |
| Arabitol | Saccharomyces rouxii, S. mellis, Sclerotium glucanicum, Pichia ohmeri | Gutcho, Chemicals by Fermentation, Noyes Data Corporation (1973), |
| Xylitol | Saccharomyces cerevisiae | Gutcho, Chemicals by Fermentation, Noyes Data Corporation (1973), |
| Hyaluronic acid | Streptococcus sp. | Rehm, H.-J.: Biotechnology, Weinheim, VCH, 1980 and 1993-1995; |
| Trehalose | Brevibacterium, Corynebacterium, Microbacterium, Arthrobacter spp., Pleurotusgenus, Filobasidium floriforme | JP 05099974, JP 06311891, FR 2671099, EP 0555540, JP 3053791, Miyazaki, J.-I., Miyagawa, K.-I., Sugiyama, Y.: Trehalose Accumulation by Basidiomycotinous Yeast, Filobasidium floriforme. Journal of Fermentation and Bioengineering 81, (1996) 4, 315-319. |
| Ascorbic acid | Gluconobacter melanogenes | RÖMPP Online Version 2.2 |
| Vitamin $B_{12}$ | Propionibacterium spp., Pseudomonas denitrificans | Chem. Ber. 1994, 923-927; RÖMPP Online Version 2.2 |
| Riboflavin | Bacillus subtilis, Ashbya gossypii | WO 01/011052, DE 19840709, WO 98/29539, EP 1186664; Fujioka, K.: New biotechnology for riboflavin (vitamin $B_2$) and character of this riboflavin. Fragrance Journal (2003), 31(3), 44-48. |
| Vitamin $B_6$ | Rhizobium tropici, R. meliloti | EP0765939 |
| Enzymes | Aspergilli (for example Aspergillus niger A. oryzae), Trichoderma, E. coli, Hansenula or Pichia (for example Pichia pastorius), Bacillus (for example Bacillus licheniformis B. subtilis) and many others | Rehm, H.-J.: Biotechnology, Weinheim, VCH, 1980 and 1993-1995; Gutcho, Chemicals by Fermentation, Noyes Data Corporation (1973), |
| Zeaxanthin | Dunaliella salina | Jin et al (2003) Biotech.Bioeng. 81: 115-124 |
| Canthaxanthin | Brevibacterium | Nelis et al (1991) J Appl Bacteriol 70: 181-191 |
| Lycopene | Blakeslea trispora, Candida utilis | WO 03/056028, EP 01/201762, WO 01/12832, WO 00/77234, Miura et al (1998) Appl Environ Microbiol 64: 1226-1229 |

TABLE A-continued

| Substance | Microorganism | Reference |
|---|---|---|
| β-Carotene | *Blakeslea trispora*, *Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia rhodozyma*; *Candida utilis* | U.S. Pat. No. 5,599,711; WO 91/02060, Miura et al (1998) Appl Environ Microbiol 64: 1226-1229 |
| Polyhydroxyalkanoates, polyesters | *Escherchia coli*, *Alcaligenes latus*, and many others | S. Y. Lee, Plastic Bacteria, Progress and prospects for polyhydroxyalkanoate production in bacteria, Tibtech, Vol. 14, (1996), pp. 431-438., Steinbüchel, 2003; Steinbüchel (Ed.), Biopolymers, 1st ed., 2003, Wiley-VCH, Weinheim and references cited therein |
| Polysaccharides | *Leuconostoc mesenteroides*, *L. dextranicum*, *Xanthomonas campestris*, and many others | Rehm, H.-J.: Biotechnology, Weinheim, VCH, 1980 and 1993-1995; Gutcho, Chemicals by Fermentation, Noyes Data Corporation (1973), |
| Polyisoprenoids | *Lactarius* sp., *Hygrophorus* sp., *Russula* sp. | Steinbüchel (Ed.), Biopolymers, 1st ed., 2003, Wiley-VCH, Weinheim and references cited therein |
| Acetone | *Clostridium* (for example *Clostridium acetobutylicum*, *C. propionicum*) | Rehm, H.-J.: Biotechnology, Weinheim, VCH, 1980 and 1993-1995; Gutcho, Chemicals by Fermentation, Noyes Data Corporation (1973), |
| Acetoin | *Enterobacter aerogenes*, *Clostridium acetobutylicum*, *Lactococcus lactis* | Lengeler, J. W., Drews, G., Schlegel, H. G.: Eds., Biology of the Procaryotes, Thieme, Stuttgart (1999), p. 307; RÖMPP Online-Edition |
| Vanillin | *Pseudomonas putida*, *Amycolatopsis* sp. | Priefert, H., Rabenhorst, J., Seinbüchel, A. Biotechnological production of vanillin. Appl. Microbiol. Biotechnol. 56, 296-314 (2001) |
| Thuringensin | *Bacillus thuringiensis* | Jian-Zhong Jong et al.: Fed-batch culture of *Bacillus thuringiensis* for thuringensin production in a tower type bioreactor. Biotechnology and Bioengineering 48 (3) (2004), 207-213. |
| Polyketides | *Streptomyces fradiae*, *Sorangium cellulosum* | Kirst: Fermentation-derived compounds as a source for new products. Pure & Appl. Chem. 70 (2), (1998), 335-338; Zirkle et al.: Heterologous production of the antifungal polyketide antibiotic soraphen A of *Sorangium cellulosum* So ce26 in *Streptomyces lividans*. Microbiology 150 (8), (2004), 2761-74. |
| Gibberellic acid | *Gibberella fujikuroi* | Hollmann et al.: Extractive fermentation of Gibberellic acid using *Gibberella fujikuroi*. CIT 7 (1995), 892-895. |
| Indigo | *Escherichia coli* JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

In preferred embodiments of the invention, the organic compound which has been produced is selected among mono-, di- and tricarboxylic acids which optionally have hydroxyl groups attached to them and which have 3 to 10 C atoms, among proteinogenic and nonproteinogenic amino acids, purine bases, pyrimidine bases; nucleosides, nucleotides, lipids; saturated and unsaturated fatty acids; diols having 4 to 10 C atoms, polyhydric alcohols having 3 or more hydroxyl groups, long-chain alcohols having at least 4 C atoms, carbohydrates, aromatic compounds, vitamins, provitamins, cofactors, nutraceuticals, proteins, carotenoids, ketones having 3 to 10 C atoms, lactones, biopolymers and cyclodextrins.

A first preferred embodiment of the invention relates to the use of the sugar-comprising liquid medium which can be obtained in accordance with the invention in a fermentative production of enzymes such as phytases, xylanases or glucanases.

A second preferred embodiment of the invention relates to the use of the sugar-comprising liquid medium which can be obtained in accordance with the invention in a fermentative production of amino acids such as lysine, methionine, threonine and glutamate.

A further preferred embodiment of the invention relates to the use of the sugar-comprising liquid medium which can be obtained in accordance with the invention in a fermentative production of vitamins such as pantothenic acid and riboflavin, and their precursors and derivatives.

An especially preferred embodiment of the invention relates to the fermentative production of
  mono-, di- and tricarboxylic acids, in particular aliphatic mono-, di- and tricarboxylic acids having 3 to 10 C atoms, such as propionic acid, fumaric acid, succinic acid, itaconic acid, citric acid and dimethylmalonic acid,
  aliphatic hydroxycarboxylic acids having 3 to 10 C atoms, such as lactic acid and 3-hydroxypropionic acid;

long-chain alkanols as mentioned above, in particular alkanols having 4 to 10 C atoms, such as butanol;

diols as mentioned above, in particular alkanediols having 3 to 10 and in particular 3 to 8, C atoms, such as propanediol;

ketones as mentioned above, in particular ketones having 3 to 10 C atoms, such as acetone; and carbohydrates as mentioned above, in particular disaccharides such as trehalose.

In a further especially preferred embodiment, the metabolite produced by the microorganisms in the fermentation are polyhydroxyalkanoates such as poly-3-hydroxybutyrate and copolyesters with other organic hydroxycarboxylic acids such as 3-hydroxyvaleric acid, 4-hydroxybutyric acid and others which are described in Steinbüchel (loc. cit.), including for example long-chain (also referred to as longer-chain) hydroxycarboxylic acids such as 3-hydroxyoctanoic acid, 3-hydroxydecanoic acid and 3-hydroxytetradecanoic acid, and mixtures of these. To carry out the fermentation, analogous conditions and procedures as have been described for other carbon feedstocks, for example in S. Y. Lee, Plastic Bacteria Progress and prospects for polyhydroxyalkanoate production in bacteria, Tibtech, Vol. 14, (1996), pp. 431-438, may be employed.

In a preferred embodiment, the microorganisms which are employed in the fermentation are therefore selected among natural or recombinant microorganisms which overproduce at least one of the following metabolites:

enzymes such as phytase, xylanase or glucanase, in particular phytase;

amino acids such as lysine, threonine or methionine, in particular lysine and methionine;

vitamins such as pantothenic acid and riboflavin; and their precursors and/or derivatives;

disaccharides such as trehalose;

aliphatic mono-, di- and tricarboxylic acids having 3 to 10 C atoms, such as propionic acid, fumaric acid, succinic acid, itaconic acid, citric acid and dimethylmalonic acid;

polyhydroxyalkanoates such as poly-3-hydroxybutyrate and copolyesters of 3-hydroxybutyric acid;

aliphatic hydroxycarboxylic acids having 3 to 10 C atoms such as lactic acid and 3-hydroxypropionic acid;

ketones having 3 to 10 C atoms such as acetone;

alkanols having 4 to 10 C atoms such as butanol; and alkanediols having 3 to 8 C atoms such as propanediol.

Suitable microorganisms are usually selected among the genera *Corynebacterium, Bacillus, Ashbya, Escherichia, Aspergillus, Alcaligenes, Actinobacillus, Anaerobiospirillum, Lactobacillus, Propionibacterium, Rhizopus* and *Clostridium*, in particular among strains of *Corynebacterium glutamicum, Bacillus subtilis, Ashbya gossypii, Escherichia coli, Aspergillus niger* or *Alcaligenes latus, Anaerobiospirillum succiniproducens, Actinobacillus succinogenes, Lactobacillus delbruckii, Lactobacillus leichmannii, Propionibacterium arabinosum, Propionibacterium schermanii, Propionibacterium freudenreichii, Clostridium propionicum, Clostridium formicoaceticum, Clostridium acetobutylicum, Rhizopus arrhizus* and *Rhizopus oryzae*.

In a preferred embodiment, the microorganism employed in the fermentation is a strain of the genus *Corynebacterium*, in particular a strain of *Corynebacterium glutamicum*. In particular, it is a strain of the genus *Corynebacterium*, specifically of *Corynebacterium glutamicum*, which overproduces an amino acid, specifically lysine, methionine or glutamate.

In a further preferred embodiment, the microorganism employed in the fermentation is a strain of the genus *Escherichia*, in particular a strain of *Escherichia coli*. In particular, it is a strain of the genus *Escherichia*, specifically of *Escherichia coli*, which overproduces an amino acid, specifically lysine, methionine or threonine.

In a specific preferred embodiment, the metabolite produced by the microorganisms in the fermentation is lysine. To carry out the fermentation, analogous conditions and procedures as have been described for other carbon feedstocks, for example in Pfefferle et al., loc. cit. and U.S. Pat. No. 3,708,395, can be employed. In principle, both a continuous and a discontinuous (batch or fed-batch) mode of operation are suitable, with the fed-batch mode of operation being preferred.

In a further especially preferred embodiment, the metabolite produced by the microorganisms in the fermentation is methionine. To carry out the fermentation, analogous conditions and procedures as have been described for other carbon feedstocks, for example in WO 03/087386 and WO 03/100072, may be employed.

In a further especially preferred embodiment, the metabolite produced by the microorganisms in the fermentation is pantothenic acid. To carry out the fermentation, analogous conditions and procedures as have been described for other carbon feedstocks, for example in WO 01/021772, may be employed.

In a further especially preferred embodiment, the metabolite produced by the microorganisms in the fermentation is riboflavin. To carry out the fermentation, analogous conditions and procedures as have been described for other carbon feedstocks, for example in WO 01/011052, DE 19840709, WO 98/29539, EP 1 186 664 and Fujioka, K.: New biotechnology for riboflavin (vitamin B2) and character of this riboflavin. Fragrance Journal (2003), 31(3), 44-48, may be employed.

In a further especially preferred embodiment, the metabolite produced by the microorganisms in the fermentation is fumaric acid. To carry out the fermentation, analogous conditions and procedures as have been described for other carbon feedstocks, for example in Rhodes et al, Production of Fumaric Acid in 20-L Fermentors, Applied Microbiology, 1962, 10 (1), 9-15, may be employed.

In a further especially preferred embodiment, the metabolite produced by the microorganisms in the fermentation is succinic acid. To carry out the fermentation, analogous conditions and procedures as have been described for other carbon feedstocks, for example in Int. J. Syst. Bacteriol. 26, 498-504 (1976); EP 249773 (1987), to Lemme & Datta; U.S. Pat. No. 5,504,004 (1996), to Guettler, Jain & Soni; Arch. Microbiol. 167, 332-342 (1997); Guettler M V, Rumler D, Jain M K., *Actinobacillus succinogenes* sp. nov., a novel succinic-acid-producing strain from the bovine rumen. Int J Syst Bacteriol. 1999 January; 49 Pt 1:207-16; U.S. Pat. No. 5,723,322, U.S. Pat. No. 5,573,931, U.S. Pat. No. 5,521,075, WO99/06532, U.S. Pat. No. 5,869,301 or U.S. Pat. No. 5,770,435, may be employed.

In a further especially preferred embodiment, the metabolite produced by the microorganisms in the fermentation is a phytase. To carry out the fermentation, analogous conditions and procedures as have been described for other carbon feedstocks, for example in WO 98/55599, may be employed.

The fermentation generates a fermentation liquor which, in addition to the desired microbial metabolite, essentially comprises the biomass produced during the fermentation, the nonmetabolized constituents of the liquefied starch solution and, in particular, the nonstarchy solid constituents of the starch feedstock such as, for example, fibers and nonutilized sugars, and also nonutilized buffer and nutrient salts. In the present application, this liquid medium is also referred to as fermentation liquor, the term fermentation liquor also comprising the added, dextrin-containing medium (1) in which the sugars present have only been subjected to partial or incomplete fermentative conversion, i.e. in which a partial or incomplete microbial metabolization of the utilizable sugars (for example mono- and disaccharides) has taken place.

Before the isolation or depletion of a microbial metabolite or before the removal of the volatile constituents of the fermentation liquor, a sterilization step is, if, appropriate, carried out in the above-described manner.

A specific embodiment (I) of the invention relates to a process in which at least one microbial metabolite is depleted or isolated from the fermentation liquor. Most of the volatile constituents of the fermentation liquor are subsequently removed, giving rise to a solid or semisolid protein composition. A more detailed description for carrying out such a process, and of the protein composition obtained, is subject matter of WO 2005/116228 (PCT/EP2005/005728) of the applicant company, which is referred to with regard to further details.

The isolation or depletion of the metabolites from the fermentation liquor is usually carried out in such a way that at least one metabolite is depleted or isolated from the fermentation liquor so that the content of this metabolite in the fermentation liquor which remains amounts to not more than 20% by weight, in particular not more than 10% by weight, specifically not more than 5% by weight and very specifically not more than 2.5% by weight, in each case based on the total weight of the remaining fermentation liquor.

Fine chemicals (i.e. the microbial metabolite) can be isolated or depleted from the fermentation liquor in one or more steps. An essential step in this context is the removal of the solid constituents from the fermentation liquor. This can be carried out either before or after isolation of the product of value. Methods conventionally used in the art which also comprise steps for the rough cleaning and the fine purification of the products of value and for formulation are known both for the isolation of products of value and for the removal of solids, i.e. solid-liquid phase separation (for example described in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH).

To isolate the product of value, a procedure can advantageously be followed in which the solid constituents are first removed from the fermentation liquor, for example by means of centrifugation or filtration, and the product of value is subsequently isolated from the liquid phase, for example by crystallization, precipitation, adsorption or distillation. As an alternative, the product of value can also be isolated directly from the fermentation liquor, for example by using chromatographic methods or extractive methods. A chromatographic method which must be mentioned in particular is ion-exchange chromatography, where the product of value can be isolated selectively on the chromatography column. In this case, the removal of the solids from the fermentation liquor which remains is advantageously carried out for example by decanting, evaporation and/or drying.

In the case of volatile or oily compounds, it is, as a rule, necessary to monitor the maximum temperatures during processing, in particular during drying. These compounds can advantageously also be prepared by formulating them in pseudo-solid form on adsorbents. Adsorbents which are suitable for this purpose are detailed for example in WO 2005/116228 (PCT/EP2005/005728) of the applicant company. Examples of compounds which can advantageously be prepared in this manner are γ-linolenic acid, dihomo-γ-linolenic acid, arachidonic acid, eicosapentaenoic acid and docosahexaenoic acid, furthermore propionic acid, lactic acid, propanediol, butanol and acetone. These compounds in pseudo-solid formulation are also understood as being, for the purposes of the present invention, nonvolatile microbial metabolites in solid form.

A further specific embodiment (II) relates to a process in which the volatile constituents of the fermentation liquor are substantially removed, without previously isolating or depleting a nonvolatile microbial metabolite, and, if appropriate, without previously removing solid constituents, giving rise to a solid formulation of a nonvolatile microbial metabolite. A more detailed description for carrying out such a process can be found in PCT/EP2006/066057 (the earlier patent application DE 102005042541.0) of the applicant company.

"Substantially" means that, once the volatile constituents have been removed, a solid or at least semisolid residue remains which can, if appropriate, be converted into a solid product by addition of solids. As a rule, this means the removal of the volatile constituents down to a residual moisture content of not more than 30% by weight, frequently not more than 20% by weight and in particular not more than 15% by weight. As a rule, the volatile constituents of the fermentation liquor will advantageously be removed from the fermentation liquor down to a residual moisture content in the range of from 0.2 to 30% by weight, preferably 1 to 20% by weight, especially preferably 2 to 15% by weight and very especially preferably 5 to 15% by weight, based on the total weight of the solid constituents determined after drying. The residual moisture content can be determined by conventional methods with which the skilled worker is familiar, for example by means of thermogravimetry (Hemminger et al., Methoden der thermischen Analyse [Methods of thermal analysis], Springer Verlag, Berlin, Heidelberg, 1989).

Obtaining the nonvolatile metabolite(s) in solid form from the fermentation liquor can be effected in one, two or more steps, in particular in one- or two-step procedures. As a rule, at least one step, in particular the final step, for obtaining the metabolite in solid form will comprise a drying step.

In the one-step procedure, the volatile constituents of the fermentation liquor will be removed, if appropriate after aforementioned preliminary removal, until the desired residual moisture content is reached.

In the two- or multi-step procedure, the fermentation liquor will first be concentrated, for example by filtration (microfiltration, ultrafiltration) or thermally by evaporating a part of the volatile constituents. The amount of volatile constituents which are removed in this step amounts, as a rule, to 10 to 80% by weight and in particular 20 to 70% by weight, based on the total weight of the volatile constituents of the fermentation liquor. In one or more subsequent steps, the remaining volatile constituents of the fermentation liquor are removed until the desired residual moisture content has been reached.

In accordance with this embodiment (II), the volatile constituents are essentially removed from the liquid medium without previous depletion or indeed isolation of the product of value. As a consequence, when removing the volatile constituents of the fermentation liquor, the nonvolatile metabolite is essentially not removed together with the volatile constituents of the liquid medium, but remains in the resulting residue together with at least a part, usually with most and in particular with all of the other solid constituents from the fermentation liquor. Accordingly, however, it is also possible to remove—preferably small—amounts of the desired nonvolatile microbial metabolite, as a rule not more than 20% by weight, for example 0.1 to 20% by weight, preferably not more than 10, in particular not more than 5% by weight, especially preferably not more than 2.5% by weight and very especially preferably not more than 1% by weight, based on the total dry weight of the metabolite, together with the volatile constituents of the fermentation liquor when removing these constituents. In a very especially preferred embodiment, the desired nonvolatile microbial metabolite remains to at least 90% by weight, in particular at least 95% by weight, specifically 99% by weight and very specifically approximately 100% by weight, in each case based on the total dry weight of the metabolite, as solid in mixture with the portion of the solid constituents of the fermentation medium which has been obtained after removal of the volatile constituents, or with all of the solid constituents of the fermentation medium.

If desired, a portion, for example 5 to 80% by weight and in particular 30 to 70% by weight, of the nonstarchy solid constituents can be separated from the fermentation liquor, for example by means of centrifugation or filtration, before the volatile constituents are removed. If appropriate, such a preliminary separation will be carried out in order to remove coarser solids particles which comprise no, or only small amounts of, nonvolatile microbial metabolite. This preliminary filtration can be carried out using conventional methods which are known to the skilled worker, for example using coarse sieves, nets, perforated sheets or the like. If appropriate, coarse solids particles may also be separated off in a centrifugal-force separator. The equipment employed here, such as decanters, centrifuges, sedicanters and separators are also known to the skilled worker. In this manner, a solid or semisolid, for example pasty, residue is obtained which comprises the nonvolatile metabolite and the nonvolatile, generally solid, nonstarchy constituents of the starch feedstock or at least large portions thereof, frequently at least 90% by weight or all of the solid nonstarchy constituents.

The properties of the dry metabolite, which is present together with the solid constituents of the fermentation, can be formulated in a manner known per se specifically with regard to a variety of parameters such as active substance content, particle size, particle shape, tendency to dust, hygroscopicity, stability, in particular storage stability, color, odor, flowing behavior, tendency to agglomerate, electrostatic charge, sensitivity to light and temperatures, mechanical stability and redispersibility, by addition of formulation auxiliaries such as carrier and coating materials, binders and other additives.

The formulation auxiliaries which are conventionally used include, for example, binders, carrier materials, powdering/flow adjuvants, furthermore color pigments, biocides, dispersants, antifoams, viscosity regulators, acids, alkalis, antioxidants, enzyme stabilizers, enzyme inhibitors, adsorbates, fats, fatty acids, oils or mixtures of these. Such formulation auxiliaries are advantageously employed as drying aids in particular when using formulation and drying methods such as spray drying, fluidized-bed drying and freeze-drying. Further details can be found in PCT/EP2006/066057 (earlier application DE 102005042541.0).

The amount of the abovementioned additives and, if appropriate, further additives such as coating materials can vary greatly, depending on the specific requirements of the metabolite in question and on the properties of the additives employed and can be for example in the range of from 0.1 to 80% by weight and in particular in the range of from 1 to 30% by weight, in each case based on the total weight of the product or substance mixture in its finished formulated form.

The addition of formulation auxiliaries can be effected before, during or after working up the fermentation liquor (also referred to as product formulation or solids design), in particular during drying. An addition of formulation auxiliaries before working up the fermentation liquor or the metabolite can be advantageous in particular for improving the processibility of the substances or products to be worked up. The formulation auxiliaries can be added either to the metabolite obtained in solid form or else to a solution or suspension comprising the metabolite, for example directly to the fermentation liquor after the fermentation has been completed or to a solution or suspension obtained during work-up and before the final drying step.

Thus, for example, the auxiliaries can be admixed with a suspension of the microbial metabolite; such a suspension can also be applied to a carrier material, for example by spraying on or mixing in. The addition of formulation auxiliaries during drying can be of importance for example when a solution or suspension comprising the metabolite is being sprayed. An addition of formulation auxiliaries is effected in particular after drying, for example when applying coatings/coating layers to dried particles. Further auxiliaries can be added to the product both after drying and after an optional coating step.

Removing the volatile constituents from the fermentation liquor is effected in a manner known per se by customary methods for separating solid phases from liquid phases, including filtration methods and methods of evaporating volatile constituents of the liquid phases. Such methods, which may also comprise steps for roughly cleaning the products of value and formulation steps, are described, for example in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH. Methods, equipment, auxiliaries and general or specific embodiments which are known to the skilled worker which can be employed within the scope of product formulation or work-up after the fermentation has ended are furthermore described in EP 1038 527, EP 0648 076, EP 835613, EP 0219 276, EP 0394 022, EP 0547 422, EP 1088 486, WO 98/55599, EP 0758 018 and WO 92/12645.

In a first variant of this embodiment (II), the nonvolatile microbial metabolite, if present in dissolved form in the liquid phase, will be converted from the liquid phase into the solid phase, for example by crystallization or precipitation. Thereafter, the nonvolatile solid constituents, including the metabolite, are separated, for example by means of centrifugation, decanting or filtration. Oily metabolites may also be separated off in a similar manner, the oily fermentation products in question being converted into a solid form by addition of adsorbents, for example silica, silica gels, loam, clay and active charcoal.

In a second variant of this embodiment (II), the volatile constituents are removed by evaporation. The evaporation can be effected in a manner known per se. Examples of suitable methods for evaporating volatile constituents are spray drying, fluidized-bed drying or fluidized-bed agglomeration, freeze drying, pneumatic driers and contact driers, and extrusion drying. A combination of the abovementioned methods with shape-imparting methods such as extrusion, pelleting or prilling may also be carried out. In these last-mentioned methods, it is preferred to employ partially or largely pre-dried metabolite-comprising substance mixtures.

In a preferred embodiment, the removal of the volatile constituents of the fermentation liquor comprises a spray-drying method or a fluidized-bed drying method, including fluidized-bed granulation. To this end, the fermentation liquor, if appropriate after a preliminary separation for removing coarse solids particles which comprise only small amounts of nonvolatile microbial metabolite, if any, is fed to one or more spray-drying or fluidized-bed-drying apparatuses. The transport, or feeding, of the solids-loaded fermentation liquor is expediently effected by means of customary transport devices for solid-comprising liquids, for example pumps, such as eccentric screw pumps (for example from Delasco PCM) or high-pressure pumps (for example from LEWA Herbert Ott GmbH).

A fermentation using the sugar-containing liquid medium according to the invention can also be carried out in such a way that
(i) a portion of not more than 50% by weight, for example in the range of from 5 to 45% by weight, based on the total weight, is removed from the dextrin-containing medium (1) obtained in step a2), which comprises nonstarchy solid constituents of the starch feedstock, and the remainder is supplied to a fermentation for the production of a first metabolite (A), for example a nonvolatile metabolite (A) in solid form or a volatile metabolite (A); and
(ii) this portion, if appropriate after previously having removed all or some of the nonstarchy solid constituents of the starch feedstock, is supplied to a fermentation for the production of a second metabolite (B), which is identical to, or different from, the metabolite (A).

If the nonstarchy solid constituents of (ii) are separated, the solids content of the remaining portion of the sugar-comprising liquid medium amounts to preferably not more than 50% by weight, in particular not more than 30% by weight, especially preferably not more than 10% by weight and very especially preferably not more than 5% by weight. In such a case, it is particularly preferred to separate all of the solids before the fermentation for the production of the second metabolite (B).

This procedure makes possible, in the separate fermentation of (ii), the use of microorganisms for which certain minimum requirements, for example with regard to the oxygen transfer rate, must be met. Suitable microorganisms which are employed in the separate fermentation of (ii) are, for example, *Bacillus* species, preferably *Bacillus subtilis*. The compounds produced by such microorganisms in the separate fermentation are selected in particular from vitamins, cofactors and nutraceuticals, purine and pyrimidine bases, nucleosides and nucleotides, lipids, saturated and unsaturated fatty acids, aromatic compounds, proteins, carotenoids, specifically from vitamins, cofactors and nutraceuticals, proteins and carotenoids, and very specifically from riboflavin and calcium pantothenate.

A preferred embodiment of this procedure relates to parallel production of identical metabolites (A) and (B) in two separate fermentations. This is advantageous in particular in a case where different applications of the same metabolite have different purity requirements. Accordingly, the first metabolite (A), for example an amino acid to be used as feed additive, for example lysine, methionine, threonine or glutamate, is produced using the solids-containing fermentation liquor and the same second metabolite (B), for example the same amino acid to be used as food additive, is produced using the solids-depleted fermentation liquor of (ii). Owing to the complete or partial removal of the nonstarchy solid constituents, the complexity of the purification when working up the metabolite whose field of application has a higher purity requirement, for example as food additive, can be reduced.

In a further preferred embodiment, this procedure can be carried out for example as follows. A preferably large-volume fermentation for the production of metabolites A, for example amino acids such as lysine, methionine, glutamate or threonine, of citric acid or of ethanol, is implemented, for example in accordance with the processes described in WO 2005/116228 (PCT/EP2005/005728) or PCT/EP2006/066057 (the earlier patent application DE 102005042541.0), or in accordance with the known methods of the fermentative production of bioethanol. In accordance with i), some of the medium (1) obtained in step a2) is removed. The portion removed in accordance with i) can be freed in accordance with ii) completely or in part from the solids by customary methods, for example centrifugation or filtration, depending on what is required in the fermentation for the production of B. The medium (1) obtained in this way, which is, if appropriate, fully or partially freed from the solids, is, in accordance with ii), supplied to a fermentation for the production of a metabolite B, A solids stream separated in accordance with i) is advantageously returned to the stream of the medium (1) of the large-volume fermentation.

If the microbial metabolite (A) which is produced in the large-volume fermentation is ethanol, the medium (1) prepared in accordance with step ii) has oligosaccharide concentrations as are customary in the fermentative production of ethanol (bioethanol), for example in the range of from 20 to 33% by weight. Again, removing solids in accordance with step ii) depends on what is required in the fermentation for the production of the metabolite B in question.

In a preferred embodiment of the abovedescribed procedure, the metabolite B produced by the microorganisms in the fermentation is riboflavin. To carry out the fermentation, analogous conditions and procedures as have been described for other carbon feedstocks, for example in WO 01/011052, DE 19840709, WO 98/29539, EP 1186664 and Fujioka, K.: New biotechnology for riboflavin (vitamin B2) and character of this riboflavin. Fragrance Journal (2003), 31(3), 44-48, can be employed.

To carry out this variant of the process, a preferably large-volume fermentation is implemented for the production of metabolites A, for example of amino acids such as lysine, methionin or glutamate, or of citric acid or of ethanol, as described above. In accordance with i), some of the medium (1) obtained in step a2) is removed and freed in accordance with ii) completely or in part from the solids by customary methods, for example centrifugation or filtration. The medium (1) obtained therefrom, which is essentially fully or partially freed from the solids, is, in accordance with ii), supplied to a fermentation for the production of metabolite B, in the present case riboflavin. The solids stream separated in accordance with ii) is advantageously returned to the stream of the medium (1) of the large-volume fermentation.

The riboflavin-containing fermentation liquor which is thus generated can be worked up by analogous conditions and procedures as have been described for other carbon feedstocks, for example in DE 4037441, EP 464582, EP 438767 and DE 3819745. Following lysis of the cell mass, the riboflavin, which is present in crystalline form, is separated, preferably by decanting. Other ways of separating solids, for example filtration, are also possible. Thereafter, the riboflavin is dried, preferably by means of spray dryers and fluidized-bed dryers. As an alternative, the riboflavin-containing fermentation mixture produced in accordance with ii) can be worked up by analogous conditions and procedures as described in, for example, EP 1048668 and EP 730034. After pasteurization, the fermentation liquor is centrifuged, and the remaining solids-containing fraction is treated with a mineral acid. The riboflavin formed is removed from the aqueous-acidic medium by filtration, washed, if appropriate, and subsequently dried.

In a further preferred embodiment of this procedure, the metabolite B produced by the microorganisms in the fermentation is pantothenic acid. To carry out the fermentation, analogous conditions and procedures as have been described for other carbon feedstocks, for example in WO 01/021772, can be employed.

To carry out this process variant, a procedure such as described above for riboflavin may be followed. The medium (1) which has been subjected to a preliminary purification in accordance with i) and which has preferably been essentially freed from the solids is supplied to a fermentation in accordance with ii) for the production of pantothenic acid. Here, the fact that the viscosity is reduced in comparison with the solids-containing liquid medium is particularly advantageous. The separated solids stream is preferably returned to the stream of the sugar-containing liquid medium (1) of the large-volume fermentation.

The pantothenic-acid-containing fermentation liquor produced in accordance with ii) can be worked up by analogous conditions and procedures as have been described for other carbon feedstocks, for example in EP 1 050 219 and WO 01/83799. After all of the fermentation liquor has been pasteurized, the remaining solids are separated, for example by centrifugation or filtration. The clear runoff obtained in the solids separation is partly evaporated, if appropriate treated with calcium chloride and dried, in particular spray dried.

The solids which have been separated off can be obtained together with the respective desired microbial metabolite (A) within the scope of the parallel large-volume fermentation process.

After the drying and/or formulation, whole or milled cereal kernels, preferably maize, wheat, barley, millet, triticale and/or rye, may be added to the product formulation or protein composition.

The examples which follow are intended to illustrate individual aspects of the present invention, but are in no way to be understood as limiting.

EXAMPLES

I. Milling the Starch Feedstock

The millbases employed hereinbelow were produced as follows. Whole maize kernels were ground completely using a rotor mill. Using different beaters, milling paths or screen elements, three different degrees of fineness were obtained. A screen analysis of the millbase by means of a laboratory vibration screen (vibration analyzer: Retsch Vibrotronic type VE1; screening time 5 minutes, amplitude: 1.5 mm) gave the results listed in Table 1.

TABLE 1

| | Experiment number | | |
|---|---|---|---|
| | T 70/03 | T 71/03 | T 72/03 |
| <2 mm/% | 99.4 | 100 | 100 |
| <0.8 mm/% | 66 | 100 | 99 |
| <0.63 mm/% | 58.6 | 98.5 | 91 |
| <0.315 mm/% | 48.8 | 89 | 65 |
| <0.1 mm/% | | 25 | 9.6 |
| <0.04 mm/% | | 8 | 3.2 |
| Millbase amount in total | 20 kg | 11.45 kg | 13.75 kg |

II. Enzymatic Starch Liquefaction and Starch Saccharification

II.1. Without Phytase in the Saccharification Step
II.1a) Enzymatic Starch Liquefaction 320 g of dry-milled maize meal (T71/03) were suspended in 480 g of water and admixed with 310 mg of calcium chloride by continuous stirring. Stirring was continued during the entire experiment. After the pH was brought to 6.5 with $H_2SO_4$ and the mixture had been heated to 35° C., 2.4 g of Termamyl 120L type L (Novozymes A/S) were added. In the course of 40 minutes, the reaction mixture was heated to a temperature of 86.5° C., the pH being readjusted with NaOH to the previously set value, if appropriate. Within 30 minutes, a further 400 g of the dry-milled maize meal (T71/03) were added, during which process the temperature was raised to 91° C. The reaction mixture was held at this temperature for approximately 100 minutes. A further 2.4 g of Termamyl 120L were subsequently added and the temperature was held for approximately 100 minutes. The progress of the liquefaction was monitored during the experimentation using the iodine-starch reaction. The temperature was finally raised to 100° C. and the reaction mixture was boiled for a further 20 minutes. At this point in time, starch was no longer detectable. The reactor was cooled to 35° C.

II.3 Further Protocols for the Enzymatic Liquefaction of Starch
II.3a) Maize Meal 360 g of deionized water were introduced into a reaction vessel. 1.54 ml of $CaCl_2$ stock solution (100 g $CaCl_2 \times 2H_2O$/l) were added to the mash to a final concentration of approximately 70 ppm $Ca^{2+}$. 240 g of corn meal were slowly run into the water, with constant stirring. After the pH has been brought to 6.5 using 50% by weight strength aqueous NaOH solution, 4.0 ml (=2% by weight enzyme/dry matter) of Termamyl 120 L type L (Novozymes A/S) were added. The mash was then heated rapidly up to 85° C. During this process, it was necessary to constantly monitor and, if appropriate, adjust the pH.

After the final temperature had been reached, further meal was added, initially 50 g of meal. In addition, 0.13 ml of $CaCl_2$ stock solution was added to the mash in order to maintain the $Ca^{2+}$ concentration at 70 ppm. During the addition, the temperature was held at a constant 85° C. At least 10 minutes were allowed to pass in order to ensure a complete reaction before a further portion (50 g of meal and 0.13 ml of $CaCl_2$ stock solution) were added. After the addition of two portions, 1.67 ml of Termamyl were added; thereafter, two further portions (in each case 50 g of meal and 0.13 ml of $CaCl_2$ stock solution) were added. A dry matter content of 55% by weight was obtained. After the addition, the temperature was raised to 100° C., and the mash was boiled for 10 minutes.

A sample was taken and cooled to room temperature. After the sample has been diluted with deionized water (approximately 1:10), one drop of concentrated Lugol's solution (mixture of 5 g of iodine and 10 g of potassium iodide per liter) was added. An intense blue coloration indicated that residual starch was present; a brown coloration was observed when all of the starch had been hydrolyzed. When the test indicated that a portion of residual starch was present, the temperature was again lowered to 85° C. and kept constant. A further 1.67 ml of Termamyl were added until the iodine-starch reaction was negative.

II.3b) Rye Meal (Including Pretreatment with Cellulase/Hemicellulase)

360 g of deionized water were introduced into a reaction vessel. 155 g of rye meal were slowly run into the water, with constant stirring. The temperature was maintained at a constant 50° C. After the pH had been brought to 5.5 using 50% by weight strength of aqueous NaOH solution, 3.21 ml (=2.5% by weight enzyme/dry matter) of Viscozyme L (Novozymes A/S) were added. After 30 minutes, further meal was added, with 55 g of meal being added initially. After a further 30 minutes, a further 50 g of meal were added; 30 minutes later, a further 40 g of meal were added. 30 minutes after the last addition, the liquefaction could be started.

1.7 ml of CaCl$_2$ stock solution (100 g CaCl$_2$×2H$_2$O/l) were added. After the pH had been adjusted to 6.5 using 50% by weight of aqueous NaOH solution, 5.0 ml (=2% by weight enzyme/dry matter) of Termamyl 120 L type L (Novozymes A/S) were added. The mash was then heated rapidly to 85° C. During this process, the pH was continuously monitored and, if appropriate, adjusted.

After the final temperature had been reached, further meal was added, initially 60 g of meal. In addition, 0.13 ml of CaCl$_2$ stock solution was added to the mash in order to maintain the Ca$^{2+}$ concentration at 70 ppm. During the addition, the temperature was held at a constant 85° C. At least 10 minutes were allowed to pass in order to ensure a complete reaction before a further portion (40 g of meal and 0.1 ml of CaCl$_2$ stock solution) was added. 1.1 ml of Termamyl were added; thereafter, a further portion (40 g of meal and 0.1 ml of CaCl$_2$ stock solution) was added. A dry matter content of 55% by weight was reached. After the addition, the temperature was raised to 100° C., and the mash was boiled for 10 minutes.

A sample was taken and cooled to room temperature. After the sample has been diluted with deionized water (approximately 1:10), one drop of concentrated Lugol's solution (mixture of 5 g of iodine and 10 g of potassium iodide per liter) was added. An intense blue coloration indicated that residual starch was present; a brown coloration was observed when all of the starch had been hydrolyzed. When the test indicated that a portion of residual starch was present, the temperature was again lowered to 85° C. and kept constant. A further 1.1 ml of Termamyl were added until the iodine-starch reaction was negative.

II.3c) Wheat Meal (Including Pretreatment with Xylanase)

360 g of deionized water were introduced into a reaction vessel. The water was heated to 55° C., and the pH is adjusted to 6.0 using 50% by weight strength aqueous NaOH solution. After the temperature and the pH had been adjusted, 3.21 ml (=2.5% by weight enzyme/dry matter) of Shearzyme 500L (Novozymes A/S) were added. 155 g of wheat meal were slowly run into the solution, with constant stirring. The temperature and the pH were kept constant. After 30 minutes, further meal was added, with 55 g of meal being added initially. After a further 30 minutes, 50 g of meal were added; 30 minutes later, a further 40 g of meal were added. 30 minutes after the last addition, the liquefaction could be started.

The liquefaction was carried out as described in II.3b.

III. Strain

ATCC 13032 lysC$^{fbr}$

In some of the examples which follow, a modified *Corynebacterium glutamicum* strain, which has been described in WO 05/059144 under the name ATCC13032 lysCfbr was employed.

IV: Identification of Glucoamylase-Expressing/Producing Strains

IVa) Screening in Gene Databases

A search for glucoamylase-producing strains

1. Glycoamylase (1,4-alpha-D-glucan glucohydrolase) is classified by the following EC number EC 3.2.1.3 [1].
2. A search with the query EC 3.2.1.3 was carried out in the following databases: Brenda, Swissprot, ERGO-WIT, CAZY and PIR, resulting in each case in a list of proteins with EC 3.2.1.3.
3. The respective results lists were combined, filtered for hits of the taxonomic kingdoms Archaea, Bacteria and Fungi and sorted by species names.
4. The species which met the filter criterion of paragraph 3 and for which a glucoamylase entry was found in at least one of the databases mentioned in paragraph 2 are highly probably capable of producing glucoamylase. Specifically, they are the following species:

*Agrobacterium tumefaciens, Arxula adeninivorans, Ashbya gossypii, Aspergillus awamori, Aspergillus candidus, Aspergillus foetidus, Aspergillus fumigatus, Aspergillus kawachi, Aspergillus nidulans, Aspergillus niger, Aspergillus oryzae, Aspergillus phoenicis, Aspergillus saitoi, Aspergillus shirousami, Aspergillus terreus, Athelia rolfsii, Bacillus circulans, Bacillus stearothermophilus, Beta vulgaris, Bradyrhizobium japonicum, Burkholderia cenocepacia, Burkholderia fungorum, Burkholderia pseudomallei, Candida albicans, Candida antarctica, Candida glabrata, Candida tsukubaensis, Caulobacter crescentus, Cephalosporium charticola, Cephalosporium eichhorniae Ceratocystis paradoxa, Chaetomium thermophilum, Chlorobium tepidum, Chromobacterium violaceum, Cladosporium resinae, Clostridium* sp., *Clostridium thermocellum, Clostridium thermosaccharolyticum, Coniophora puteana, Corticium rolfsii, Corynebacterium glutamicum, Cryptococcus neoformans, Debaryomyces hansenii, Debaryomyces occidentalis, Emericella nidulans, Endomyces* sp., *Endomycopsis fibuligera, Fusarium venenatum, Haloarcula marismortui, Hormoconis resinae, Humicola grisea, Humicola lanuginosa, Hypocrea lixii, Kluyveromyces lactis, Lentinula edodes, Lipomyces kononenkoae, Magnaporthe grisea, Mesorhizobium loti, Methanocaldococcus jannaschii, Methanococcus jannaschii, Methanococcus maripaludis, Methanosarcina acetivorans, Methanosarcina barkeri, Methanosarcina mazei, Monascus rubiginosus, Monascus* sp., *Mucor rouxianus, Mycobacterium bovis, Mycobacterium leprae, Mycobacterium marinum, Mycobacterium tuberculosis, Myrothecium* sp., *Neurospora crassa, Nostoc punctiforme, Oryza sativa, Paecilomyces variotii, Penaeus japonicus, Penicillium chrysogenum, Penicillium oxalicum, Picrophilus torridus, Pseudomonas fluorescens, Pseudomonas putida, Pseudomonas syringae, Ralstonia eutropha, Ralstonia metallidurans, Rana japonica, Rhizobium leguminosarum, Rhizopus delemar, Rhizopus javanicus, Rhizopus niveus, Rhizopus oryzae, Rhizopus* sp., *Rhodococcus* sp., *Rhodopseudomonas palustris, Rhodospirillum rubrum, Saccharomyces cerevisiae, Saccharomyces diastaticus, Saccharomycopsis fibuligera, Saccharomycopsis fibuligera, Schizosaccharomyces pombe, Schwanniomyces occidentalis, Shewanella oneidensis, Sphingomonas aromaticivorans, Streptomyces coelicolor, Sulfolobus acidocaldarius, Sulfolobus solfataricus, Talaromyces emersonii, Termitomyces clypeatus, Thermoactinomyces vulgaris, Thermoanaerobacter tengcongensis, Thermoanaerobacterium thermosaccharolyticum, Thermoascus crustaceus, Thermomyces lanuginosus, Thermoproteus tenax, Thielavia terrestris, Trichoderma reesei* and *Trichosporon adeninovorans.*

IVb) Screening by Means of Shake-Flask Test and Subsequent Enzyme Activity Assay A variety of microorganisms are studied for glucoamylase activity in a shake-flask test. A medium which is suitable for this purpose is any conventional medium which is suitable for the growth of the organism and leads to expression of the glucoamylase. Suitable media are commercially available or can be prepared following published protocols (for example as described in catalogues of the American Type Culture Collection).

For example, a mixture of glucose oligomers with different chain lengths can be employed as the single carbon feedstock in a defined medium. Since no thermal hydrolysis of the oligosaccharides takes place under fermentation conditions, only strains with a glucoamylase and/or maltase activity are capable of growing in this medium. An example of a suitable substrate is Maldex 150 (Amylum Group). The screening is carried out under various fermentation conditions (pH, temperature). In order to distinguish between glucoamylase and maltase activity, the oligosaccharide composition of the mixture is analyzed before the experiment, for example using HPLC. Thus, for example, Maldex 150 has the following composition (see Table 2):

TABLE 2

Composition of Maldex 150 (Amylum Group)

| Degree of polymerization | [%] |
|---|---|
| DP1 | 1.1 |
| DP2 | 4.0 |
| DP3 | 7.4 |
| DP4 | 5.0 |
| DP5 | 4.8 |
| DP6 | 8.4 |
| DP7 | 9.6 |
| DP8 | 4.6 |
| DP9 | 3.5 |
| >DP9 | 51.6 |

A control medium with maltose and glucose is made up in accordance with this analysis. Growth and lysine production in the oligosaccharide medium which exceed the values from this control can then be unambiguously attributed to a glucoamylase activity.

An alternative to a maltodextrin mixture which can be employed as carbon feedstock for a screening would be pure maltotetraose, maltopentaose and the like. After the cultivation has been stopped, the biomass is centrifuged off and the supernatant is filtered.

The clear supernatant is employed in a glucoamylase activity assay (CHEN et al., *J. Gen. Appl. Microbiol.*, 51, 175-181 (2005)). To this end, a reaction mixture of 0.2 ml of 50 mM acetate/sodium acetate buffer (pH 5.0) and 0.5% of soluble starch and 0.2 ml of supernatant is employed for this purpose. The reaction is stopped after a reaction time of 10 minutes at 60° C. by boiling for 10 minutes at 100° C. The amount of glucose liberated is determined with the aid of the glucose oxidase/peroxidase method (Bergmayer and Bernt, 1974). In this context, one unit of glucoamylase activity is defined as the amount of enzyme which liberates 1 µmol of glucose per minute from soluble starch under the prevailing reaction conditions.

IVc) Screening with the Aid of Primers/Probes

An alternative method for testing the organism to be studied for glucoamylase-encoding sequences is a screening with the aid of primers or probes which are specific for these sequences.

i) Starting from conserved regions of known glucoamylase genes, a probe is constructed for identifying and cloning, from various organisms, DNA sequences which code for polypeptides with glucoamylase activity. Such probes can be exploited in particular for hybridization with the genomic DNA or cDNA of the desired organism, followed by a Southern blot carried out by the standard method in order to identify the desired gene.

The skilled worker will find instructions for the identification of DNA sequences by means of hybridization in the textbook "The DIG System Users Guide for Filter Hybridization" from Boehringer Mannheim GmbH (Mannheim, Germany, 1993) and in Liebl et al. (International Journal of Systematic Bacteriology (1991) 41: 255-260), inter alia.

ii) Starting from conserved regions of known glucoamylase genes, PCR primers are synthetized. These primers are employed in a PCR reaction with the DNA of the organism to be studied. If suitable binding sites for the primers, i.e. glucoamylase-encoding genes, are present, the corresponding amplified oligonucleotides can be identified with the aid of a gel electrophoresis which is subsequently carried out. The skilled worker will find instructions for the amplification of DNA sequences with the aid of the polymerase chain reaction (PCR) in the textbook by Gait: Oligonucleotide synthesis: a practical approach (IRL Press, Oxford, UK, 1984) and in Newton and Graham: PCR (Spektrum Akademischer Verlag, Heidelberg, Germany, 1994), inter alia.

Example 1

Liquefied maize meal hydrolyzate was employed in shake-flask experiments using *Corynebacterium glutamicum*.

I) Liquefaction 360 g of deionized water were introduced into a reaction vessel. 240 g of maize meal were slowly run into the water, with constant stirring. After the pH had been brought to 5.8 with 50% strength aqueous NaOH solution, 4.0 ml (=2% by weight enzyme/dry matter) of Liquozyme SC (from Novozymes A/S) were added. The mash was then heated rapidly to 85° C. During this process, the pH was checked constantly and, if appropriate, adjusted.

After the final temperature has been reached, further meal was added, initially 50 g of meal. During the addition, the temperature was held at a constant 85° C. At least 10 minutes were allowed to pass in order to ensure a complete reaction before a further portion (50 g) of meal is added. After the addition of two portions, 1.67 ml of Liquozyme were added; thereafter, two further portions (in each case 50 g) of meal were added. A dry matter content of 55% by weight was obtained. After the addition, the temperature was raised to 100° C., and the mash was boiled for 10 minutes.

A sample was taken and cooled to room temperature. After the sample has been diluted with deionized water (approximately 1:10), one drop of concentrated Lugol's solution (mixture of 5 g iodine and 10 g of potassium iodide per liter) was added. An intense blue coloration indicates that residual starch is present; a brown coloration is observed when all of the starch has been hydrolyzed. When the mixture tested negative for starch, it was filled into sterile containers while hot and, after cooling, stored at 4° C.

II) Fermentation with *Corynebacterium glutamicum* Strain

The modified wild type with feedback-deregulated aspartokinase ATCC13032 lysCfbr was used.

Preparation of the Inoculum

The cells were streaked onto sterile CM+CaAc agar (composition: see Table 3; 20 min at 121° C.) and then incubated overnight at 30° C. Thereafter, the cells were scraped from the plates and resuspended in saline. 25 ml of the medium (see Table 4) in 250-ml-Erlenmeyer flasks equipped with two baffles were inoculated in each case with such an amount of the resulting cell suspension that the optical density reached an OD610 value of 0.5 at 610 nm.

TABLE 3

Composition of the CM + CaAc agar plates

| Concentration | Constituent |
|---|---|
| 10.0 g/l | D-glucose |
| 2.5 g/l | NaCl |
| 2.0 g/l | Urea |
| 5.0 g/l | Bacto peptone (Difco) |
| 5.0 g/l | Yeast extract (Difco) |
| 5.0 g/l | Beef Extract (Difco) |
| 20.0 g/l | Casamino acids |
| 20.0 g/l | Agar |

Preparation of the Fermentation Liquor

The compositions of the flask medium is shown in Table 4. The experiment was carried out in triplicate.

TABLE 4

Flask media

| Maize meal hydrolyzate | 180 g/l |
|---|---|
| $(NH_4)_2SO_4$ | 20 g/l |
| Urea | 5 g/l |
| $KH_2PO_4$ | 0.113 g/l |
| $K_2HPO_4$ | 0.138 g/l |
| ACES | 52 g/l |
| MOPS | 21 g/l |
| Citric acid × $H_2O$ | 0.49 g/l |
| 3,4-Dihydroxybenzoic acid | 3.08 mg/l |
| NaCl | 2.5 g/l |
| KCl | 1 g/l |
| $MgSO_4 \times 7H_2O$ | 0.3 g/l |
| $FeSO_4 \times 7H_2O$ | 25 mg/l |
| $MnSO_4 \times 4\text{-}6H_2O$ | 5 mg/l |
| $ZnCl_2$ | 10 mg/l |
| $CaCl_2$ | 20 mg/l |
| $H_3BO_3$ | 150 µg/l |
| $CoCl_2 \times 6H_2O$ | 100 µg/l |
| $CuCl_2 \times 2H_2O$ | 100 µg/l |
| $NiSO_4 \times 6H_2O$ | 100 µg/l |
| $Na_2MoO_4 \times 2H_2O$ | 25 µg/l |
| Biotin (vit. H) | 1050 µg/l |
| Thiamine × HCl (vit $B_1$) | 2100 µg/l |
| Nicotinamide | 2.5 mg/l |
| Pantothenic acid | 125 mg/l |
| Cyanocobalamin (vit $B_{12}$) | 1 µg/l |
| 4-Aminobenzoic acid (PABA; vit. $H_1$) | 600 µg/l |
| Folic acid | 1.1 µg/l |
| Pyridoxin (vit. $B_6$) | 30 µg/l |
| Riboflavin (vit. $B_2$) | 90 µg/l |
| CSL | 40 ml/l |
| pH* | 6.85 |

*adjusted with dilute aqueous NaOH solution

After the inoculation, the flasks were incubated for 3 days at 30° C. and with shaking (200 rpm) in a humidified shaker.

After the fermentation was terminated, the lysine content was determined by HPLC. The HPLC analyses were carried out with an Agilent 1100 series LC system. The amino acid concentration was determined by means of high-pressure liquid chromatography on an Agilent 1100 series LC System HPLC. Pre-column derivatization with ortho-phthalaldehyde permits the quantification of the amino acids formed; the amino acid mixture is separated using an Agilent Hypersil AA column.

The results are compiled in Table 5.

TABLE 5

Lysine production (means)

| Fermentation time | Lysine [g/l] |
|---|---|
| 45 h | 11.5 |
| 70 h | 12.8 |
| Control (45 h) | 11.1 |

Example 2

Liquefied maize meal hydrolyzate was employed in shake-flask experiments using *Aspergillus niger*.

I) Liquefaction

The liquefaction was carried out as described in example 1 under 1).

II) Fermentation with *Aspergillus niger* Strain

An *Aspergillus niger* phytase production strain with 6 copies of the phyA gene from *Aspergillus ficuum* under the control of the glaA promoter was generated analogously to the preparation of NP505-7 as described in detail in WO98/46772. A strain with 3 modified glaA amplicons (analogous to ISO505), but without integrated phyA expression cassettes, was used as the control.

Preparation of the Inoculum 20 ml of the preculture medium (see Table 6) in 100-ml-Erlenmeyer flasks equipped with one baffle are each inoculated with 100 µl of a frozen culture and incubated for 24 hours at 34° C. in a humidifed shaker, with shaking (170 rpm).

TABLE 6

Composition of the preculture medium

| Constituent | Concentration |
|---|---|
| Glucose | 30.0 g/l |
| Peptone from casein | 10.0 g/l |
| Yeast Extract | 5.0 g/l |
| $KH_2PO_4$ | 1.0 g/l |
| $MgSO_4 \times 7H_2O$ | 0.5 g/l |
| $ZnCl_2$ | 30 mg/l |
| $CaCl_2$ | 20 mg/l |
| $MnSO_4 \times 1H_2O$ | 9 mg/l |
| $FeSO_4 \times 7H_2O$ | 3 mg/l |
| Tween 80 | 3.0 g/l |
| Penicillin | 50000 IU/l |
| Streptomycin | 50 mg/l |
| pH* | 5.5 |

*adjusted using dilute sulfuric acid 50 ml of the main culture medium (see Table 7) in 250-ml-Erlenmeyer flasks equipped with one baffle are each inoculated with 5 ml of preculture.

Preparation of the Fermentation Liquor

The compositions of the flask medium is shown in Table 7. Two flasks were set up for each sample.

TABLE 7

| Flask media | |
|---|---|
| Maize meal hydrolyzate | 200 g/l |
| Peptone from casein | 25.0 g/l |
| Yeast Extract | 12.5 g/l |
| $KH_2PO_4$ | 1.0 g/l |
| $K_2SO_4$ | 2.0 g/l |
| $MgSO_4 \times 7H_2O$ | 0.5 g/l |
| $ZnCl_2$ | 30 mg/l |
| $CaCl_2$ | 20 mg/l |
| $MnSO_4 \times 1H_2O$ | 9 mg/l |
| $FeSO_4 \times 7H_2O$ | 3 mg/l |
| Penicillin | 50000 IU/l |
| Streptomycin | 50 mg/l |
| pH* | 5.6 |

*to be adjusted with dilute sulfuric acid

After the inoculation, the flasks were incubated for 6 days at 34° C. in a humidified shaker, with shaking (170 rpm). After the fermentation was stopped, the phytase activity was determined at a suitable phytase activity level (standard: 0.6 U/ml) in 250 mM acetic acid/sodium acetate/Tween 20 (0.1% by weight), pH 5.5 buffer, using phytic acid as the substrate. The assay was standardized for use in microtiter plates (MTPs). 10 µl of the enzyme solution were mixed with 140 µl of 6.49 mM phytate solution in 250 mM sodium acetate buffer, pH 5.5 (phytate: dodecasodium salt of phytic acid). After incubation for one hour at 37° C., the reaction was stopped by addition of an equal volume (150 µl) of trichloroacetic acid. One aliquot of this mixture (20 µl) was transferred into 280 µl of a solution comprising 0.32 $NH_2SO_4$, 0.27% by weight of ammonium molybdate and 1.08% by weight of ascorbic acid. This was followed by incubation for 25 minutes at 50° C. The absorption of the blue solution was measured at 820 nm. The results are compiled in Table 8.

TABLE 8

| Phytase activity after the fermentation was stopped | |
|---|---|
| Flask | Phytase activity [FTU/ml] |
| 1 | 569 |
| 2 | 696 |
| Control | 393 |

We claim:

1. A process for the production of at least one organic compound having at least 3 C atoms or having at least 2 C atoms and at least one N atom, where the organic compound is selected among mono-, di- and tricarboxylic acids which optionally have hydroxyl groups attached to them and which have 3 to 10 carbon atoms, proteinogenic and nonproteinogenic amino acids, purine bases, pyrimidine bases; nucleosides, nucleotides, lipids; saturated and unsaturated fatty acids; diols having 4 to 10 carbon atoms, polyhydric alcohols having 3 or more hydroxyl groups, long-chain alcohols having at least 4 carbon atoms, carbohydrates, aromatic compounds, vitamins, provitamins, cofactors, nutraceuticals, proteins, carotenoids, ketones having 3 to 10 carbon atoms, lactones, polyhydroxyacetate, polyester, polylactide, polysaccharides, polyisoprenoids, polyamides and cyclodextrins, by means of fermentation, comprising the following steps:
   a1) milling a cereal kernels as a starch feedstock, thus obtaining a millbase which comprises at least 20% by weight of the nonstarchy solid constituents of the starch feedstock;
   a2) suspending the millbase in an aqueous liquid and liquefying the millbase present in the aqueous liquid in the presence of at least one starch-liquefying enzyme, obtaining an aqueous dextrin-containing medium (1) which comprises at least 20% by weight of all a part of the nonstarchy solid constituents of the starch feedstock; and
   b) using the aqueous dextrin-containing medium (1) in a fermentation liquor for culturing a microorganism which is capable of overproducing the organic compound and which is capable of metabolizing dextrins present in the aqueous dextrin-containing medium (1) without externally adding enzymes which hydrolyze the dextrins to monosaccharides; and
   c) optionally, enzymes which hydrolyze dextrins to monosaccharides can be added externally in an amount of less than 0.001% by weight based on the total weight of the starch feedstock employed.

2. The process according to claim 1, wherein the suspension of the millbase in the aqueous liquid is heated to a temperature above the gelatinization temperature of the starch present in the starch feedstock.

3. The process according to claim 2, wherein heating is carried out in the presence of the starch-liquefying enzyme.

4. The process according to claim 1, wherein at least one portion of the millbase is added continuously or batchwise to the aqueous liquid during the liquefaction step.

5. The process according to claim 1, wherein the millbase is suspended in such an amount in the aqueous liquid and liquefied therein that the resulting aqueous dextrin-containing medium (1) has a dry-matter content of at least 50% by weight based on the total weight of the medium (1).

6. The process according to claim 1, wherein the millbase is suspended in such an amount in the aqueous liquid and liquefied therein that the resulting aqueous dextrin-containing medium (1) has a glucose equivalent concentration of at least 40% by weight based on the total weight of the medium (1).

7. The process according to claim 1, wherein the microorganism is selected among microorganisms which produce enzymes which hydrolyze dextrins to monosaccharides.

8. The process according to claim 1, additionally comprising the following steps:
   b1) culturing, in an aqueous fermentation medium (2), the microorganism which is capable of overproducing the organic compound; and
   b2) combining the dextrin-containing medium (1) with the aqueous fermentation medium (2) to form the fermentation liquor.

9. The process according to claim 8, wherein the fermentation liquor in step b2) comprises essentially the aqueous dextrin-containing medium (1), the microorganisms which are capable of overproducing the organic compound, conventional media constituents and, optionally, water for dilution.

10. The process according to claim 8, wherein, in step b1), such an amount of the aqueous dextrin-containing medium (1) is used for making up the fermentation liquor that the total sugar concentration in the fermentation liquor is in the range from 6 to 30% by weight, calculated as glucose equivalents and based on the total weight of the fermentation medium (2).

11. The process according to claim 1, wherein the starch-liquefying enzyme is an α-amylase.

12. The process according to claim 1, wherein the microorganism employed for the fermentation is selected among natural or recombinant microorganisms which overproduce at least one of the following organic compounds: enzymes, amino acids, vitamins, disaccharides, aliphatic mono- di- and tricarboxylic acids having 3 to 10 C atoms, aliphatic hydroxycarboxylic acids having 3 to 10 C atoms, ketones having 3 to 10 C atoms, alkanols having 4 to 10 C atoms, alkanediols having 3 to 8 C atoms and polyhydroxyalkanoates.

13. The process according to claim 12, wherein the microorganism is selected among those which overproduce one or more amino acids.

14. The process according to claim 12, wherein the microorganism is selected among those which overproduce one or more aliphatic mono-, di- and tricarboxylic acids having 3 to 10 C atoms.

15. The process according to claim 12, wherein the microorganism is selected among those which overproduce one or more enzymes.

16. The process according to claim 12, wherein the microorganism is selected among those which overproduce a phytase.

17. The process according to claim 1, wherein the microorganism is selected among the genera *Corynebacterium, Bacillus, Ashbya, Escherichia, Aspergillus, Alcaligenes, Actinobacillus, Anaerobiospirillum, Lactobacillus, Propionibacterium, Clostridium* and *Rhizopus*.

18. The process according to claim 17, wherein the microorganism is selected from strains of the genus *Corynebacterium*.

19. The process according to claim 1, wherein the fermentation liquor comprises volatile constituents and wherein the process further comprises depleting or isolating at least one organic compound from the fermentation liquor and subsequently substantially removing volatile constituents of the fermentation liquor, resulting in a solid or semisolid protein composition being obtained.

20. The process according to claim 1, wherein the fermentation liquor comprises volatile constituents and wherein the process further comprises removing at least some of the volatile constituents of the fermentation liquor without previous isolation or depletion of a nonvolatile organic compound and, optionally, without previous removal of solid constituents, resulting in a solid formulation of a nonvolatile organic compound being obtained.

* * * * *